US012700086B2

(12) United States Patent
Park et al.

(10) Patent No.: US 12,700,086 B2
(45) Date of Patent: Aug. 4, 2026

(54) MEDICAL-IMAGE-BASED LESION ANALYSIS METHOD

(71) Applicant: VUNO Inc., Seoul (KR)

(72) Inventors: Hyunho Park, Seoul (KR);
Gwangbeen Park, Seoul (KR);
Seungho Lee, Seoul (KR)

(73) Assignee: VUNO Inc., Seoul (KR)

( * ) Notice: Subject to any disclaimer, the term of this patent is extended or adjusted under 35 U.S.C. 154(b) by 424 days.

(21) Appl. No.: 18/279,823

(22) PCT Filed: Mar. 2, 2022

(86) PCT No.: PCT/KR2022/002928
§ 371 (c)(1),
(2) Date: Aug. 31, 2023

(87) PCT Pub. No.: WO2022/186594
PCT Pub. Date: Sep. 9, 2022

(65) Prior Publication Data
US 2024/0144474 A1      May 2, 2024

(30) Foreign Application Priority Data

Mar. 4, 2021      (KR) ........................ 10-2021-0028533

(51) Int. Cl.
*G06T 7/00*            (2017.01)
*G06V 10/25*          (2022.01)
(Continued)

(52) U.S. Cl.
CPC ............ *G06T 7/0012* (2013.01); *G06V 10/25* (2022.01); *G06V 10/762* (2022.01);
(Continued)

(58) Field of Classification Search
CPC ......... G06T 7/0012; G06T 2207/30096; G06T 7/11; G06T 7/62; G06T 11/008;
(Continued)

(56) References Cited

U.S. PATENT DOCUMENTS 7,305,111  B2     12/2007  Arimura et al.
11,113,532  B2      9/2021  Kim et al.
(Continued)

FOREIGN PATENT DOCUMENTS

JP            2020093083  A      6/2020
KR              101981202  B1      5/2019
(Continued)

OTHER PUBLICATIONS

Machine translation obtained from Google Patents of KR 102209382B1 (Year: 2021).*

*Primary Examiner* — Courtney Joan Nelson
(74) *Attorney, Agent, or Firm* — Seed Intellectual Property Law Group LLP

(57) ABSTRACT

Disclosed is a method for analyzing a lesion based on a medical image performed by a computing device. The method may includes generating, by using a pre-processing module, an input image of a pre-trained detection module from the medical image. The method may include generating, by using the detection module, a probability value regarding a presence of a nodule in at least one region of interest and first location information about the at least one region of interest, based on the input image. The method may include determining, by using a post-processing module, second location information about a suspicious nodule present in the medical image from the first location information, based on the probability value regarding the presence of the nodule.

18 Claims, 19 Drawing Sheets

(51) Int. Cl.

| | |
|---|---|
| *G06V 10/762* | (2022.01) |
| *G06V 10/764* | (2022.01) |
| *G06V 10/771* | (2022.01) |
| *G16H 30/20* | (2018.01) |
| *G16H 50/20* | (2018.01) |

(52) U.S. Cl.
CPC .......... *G06V 10/764* (2022.01); *G06V 10/771* (2022.01); *G16H 30/20* (2018.01); *G16H 50/20* (2018.01); *G06T 2207/20084* (2013.01); *G06T 2207/30064* (2013.01); *G06T 2207/30096* (2013.01)

(58) Field of Classification Search
CPC ....... G06T 2200/04; G06T 2207/30064; G06T 7/13; G06T 2207/20076; G06T 2207/20081; G06T 2207/20084; G06T 7/0016; G16H 50/20; G16H 50/30; G16H 30/40; G16H 30/00; G16H 30/20; G06V 10/82; G06V 10/26; G06V 10/7715; G06V 2201/03; G06V 10/25; G06V 10/762; G06V 10/771; G06V 10/764; G06N 3/0464; G06N 3/045; G06N 3/02; A61B 8/085; A61B 5/4842; A61B 6/466; A61B 6/463; A61B 6/469; A61B 6/5217; A61B 8/466; A61B 8/469; A61B 8/483; A61B 8/5223
See application file for complete search history.

(56) References Cited

U.S. PATENT DOCUMENTS

| | | | |
|---|---|---|---|
| 2005/0207630 A1* | 9/2005 | Chan ..................... | G06T 7/0012 382/131 |
| 2010/0111386 A1* | 5/2010 | El-Baz ................... | G06T 7/143 382/128 |
| 2020/0160997 A1* | 5/2020 | Bagci ................... | A61B 5/7267 |
| 2020/0184639 A1 | 6/2020 | Park et al. | |
| 2020/0380675 A1 | 12/2020 | Golden et al. | |

FOREIGN PATENT DOCUMENTS

| | | | | |
|---|---|---|---|---|
| KR | 20190094133 | A | 8/2019 | |
| KR | 20200062614 | A | 6/2020 | |
| KR | 20200085012 | A | 7/2020 | |
| KR | 102150682 | B1 | 9/2020 | |
| KR | 102209382 | B1 * | 1/2021 | ........... A61B 5/0033 |

* cited by examiner

PRE-
PROCESSED
CT IMAGE

240

241

FEATURE MAP 1
(68, 68)

FEATURE MAP 2
(68, 68)

FEATURE MAP 3
(34, 34)

FEATURE MAP 4
(34, 34)

250

251

260

261

OUTPUT VALUE OF FIRST SUB
DETECTION MODULE (PROBABILITY
VALUE AND LOCATION INFORMATION)

MEDICAL-IMAGE-BASED LESION ANALYSIS METHOD

BACKGROUND

Technical Field

The present disclosure relates to a method for processing a medical image, and more particularly, to a method for detecting and measuring a lesion of a specific disease present in a medical image by using artificial intelligence.

Description of the Related Art

Medical images are data that allow physical states of various organs of the human body to be understood. The medical images include digital radiographic imaging (X-ray), computed tomography (CT), or magnetic resonance imaging (MRI).

Research and technology development on automated methods for detecting a lesion of a specific disease based on the medical images have been steadily conducted. However, conventionally developed technologies focus only on identifying lesions present in the medical images, but fail to create, process, and provide information on lesions in a form suitable for diagnosis of the specific disease. That is, from the point of view of providing necessary information suitable for diagnosis of a specific disease, the conventional technologies do not show performance suitable for the purpose of detecting and measuring the lesions.

U.S. Pat. No. 7,305,111 (Dec. 4, 2007) discloses an automated method for detecting lung nodules for lung cancer screening.

BRIEF SUMMARY

The present disclosure is contrived to correspond to the background art, and has been made in an effort to provide a method for detecting and measuring a lesion for diagnosis of a specific disease present in a medical image.

In order to realize the object, according to an embodiment of the present disclosure, disclosed is a method for analyzing a lesion based on a medical image performed by a computing device. The method may include: generating, by using a pre-processing module, an input image of a pre-trained detection module from a medical image including a chest region; generating, by using the detection module, a probability value regarding a presence of a nodule in at least one region of interest and first location information about the at least one region of interest, based on the input image; and determining, by using a post-processing module, second location information about a suspicious nodule present in the medical image from the first location information, based on the probability value regarding the presence of the nodule.

In an alternative embodiment, the generating of the input image of the detection module may include calculating a Hounsfield unit value based on a 3D medical image including the chest region by using the pre-processing module, and generating 2D medical images from the 3D medical image in which the Hounsfield unit value is calculated by using the pre-processing module.

In an alternative embodiment, the generating of the probability value regarding the presence of the nodule and the first location information may include generating a first probability value and the first location information regarding the at least one region of interest based on 2D medical images by using a first sub detection module included in the detection module, and estimating a second probability value regarding the at least one region of interest based on a 3D medical image and the first location information by using a second sub detection module included in the detection module.

In an alternative embodiment, the generating of the first probability value and the first location information may include generating first feature maps having a plurality of sizes based on the 2D medical images by using a first neural network module included in the first sub detection module, generating second feature maps by concatenating at least some of the first feature maps based on the sizes of the first feature maps by using a second neural network module included in the first sub detection module, and generating the first probability value and the first location information regarding the at least one region of interest by matching the second feature maps with a predetermined anchor box by using a third neural network module included in the first sub detection module.

In an alternative embodiment, the generating of the first probability value and the first location information may include clustering, when there is a plurality of regions of interest, at least some of the regions of interest based on a ratio of overlapping regions between the plurality of regions of interest by using the first sub detection module, and correcting a coordinate included in the first location information by using the first sub detection module.

In an alternative embodiment, the calculating of the second probability value may include generating at least one third feature map by performing encoding based on a patch extracted from the 3D medical image based on the location information by using a fourth neural network module included in the second sub detection module, generating at least one fourth feature map by performing decoding based on the third feature map by using a fifth neural network module included in the second sub detection module, and generating the second probability value regarding the at least one region of interest based on a feature map generated by combining the third feature map and the fourth feature map by using a sixth neural network module included in the second sub detection module.

In an alternative embodiment, the second sub detection module may be pre-trained by performing a first operation of training a neural network based on a randomly sampled training image, and a second operation of training the neural network based on a training image selected based on recall and precision.

In an alternative embodiment, the obtaining of the second location information about the suspicious nodule may include comparing the probability value regarding the presence of the nodule generated through a weighted sum of the first probability value and the second probability value, and a threshold value by using the post-processing module, and determining the first location information of the at least one region of interest corresponding to the probability value regarding the presence of the nodule selected as a result of the comparison as the second location information for the suspicious nodule by using the post-processing module.

In an alternative embodiment, the method may further include: generating a mask for the suspicious nodule based on a patch of the medical image corresponding to the second location information by using a pre-trained measurement module; and generating numerical information including at least one of a diameter and a volume of the suspicious nodule based on the mask for the suspicious nodule.

In an alternative embodiment, the mask for the suspicious nodule may include a first mask for entire region of the suspicious nodule generated based on a 3D patch corresponding to the second location information, and a second mask for a region representing a specific attribute of the suspicious nodule generated based on the 3D patch corresponding to the second location information.

In an alternative embodiment, the method may further include classifying a class for a state of the suspicious nodule based on the patch of the medical image and the mask for the suspicious nodule by using a pre-trained classification module.

In an alternative embodiment, the classifying of the class for the state of the suspicious nodule may include determining at least one of a type for an attribute of the suspicious nodule, whether the suspicious nodule is spiculated, or whether the suspicious nodule is calcified based on the patch and the mask by using different sub modules included in the classification module. In an alternative embodiment, the method may further include: calculating an assessment score of the suspicious nodule based on the numerical information and the class for the state of the suspicious nodule based on an auxiliary index of lung cancer diagnosis; and modifying, when a subject of the input image corresponds to a subject of a pre-analyzed image, an assessment score of the medical image or an assessment score of the pre-analyzed image based on capturing time points of the input image and the pre-analyzed image by using a pre-trained tracking module.

In an alternative embodiment, the method may further include generating a user interface based on at least one of the second location information, the mask, the class, the numerical information, or the assessment score for the suspicious nodule.

In an alternative embodiment, the method may further include estimating malignancy of the suspicious nodule based on the class for the state, the numerical information, and the second location information of the suspicious nodule, by using a pre-trained malignancy prediction module.

In an alternative embodiment, the method may further include estimating malignancy of the suspicious nodule based on the patch of the medical image and the mask for the suspicious nodule by using a pre-trained malignancy prediction module.

In an alternative embodiment, the method may further include generating a user interface based on at least one of the mask, the class, the numerical information, the malignancy, or the second location information for the suspicious nodule.

In order to realize the object, according to another embodiment of the present disclosure, disclosed is a method for analyzing a lesion based on a medical image performed by a computing device. The method may include: generating an input patch of a pre-trained measurement module based on location information of a suspicious nodule present in the medical image including a chest region; and generating a mask for the suspicious nodule based on at least one input patch corresponding to the location information by using the pre-trained measurement module.

In an alternative embodiment, the generating of the mask for the suspicious nodule may include generating a first mask for entire region of the suspicious nodule based on the at least one input patch by using a first sub measurement module included in the measurement module, and generating a second mask for a region representing a specific attribute of the suspicious nodule based on the at least one input patch by using a second sub measurement module included in the measurement module.

In an alternative embodiment, the generating of the first mask may include when input patches having a plurality of sizes for one suspicious nodule are input into the measurement module, generating first sub masks for the one suspicious nodule from respective input patches by using the first sub measurement module, and combining the first sub masks and generating the first mask for entire region of the one suspicious nodule based on a result of the combination, by using the first sub measurement module.

In an alternative embodiment, the generating of the second mask may include generating a second sub mask for a candidate region representing the specific attribute of the suspicious nodule based on the at least one input patch by using the second sub measurement module, identifying an overlapping region of the first mask and the second sub mask by using the second sub measurement module, and generating the second mask for the region representing the specific attribute of the suspicious nodule based on the identified overlapping region.

In order to realize the object, according to yet another embodiment of the present disclosure, disclosed is a method for analyzing a lesion based on a medical image performed by a computing device. The method may include: receiving a patch generated based on location information of a suspicious nodule present in the medical image including a chest region and a mask for the suspicious nodule; and classifying a class for a state of the suspicious nodule based on the patch and the mask by using a pre-trained classification module.

In an alternative embodiment, the classifying of the class for the state of the suspicious nodule may include at least one of determining a type for an attribute of the suspicious nodule based on the patch and the mask by using a first sub classification module included in the classification module, determining whether the suspicious nodule is spiculated based on the patch and the mask by using a second sub classification module included in the classification module, or determining whether the suspicious nodule is calcified based on the patch and the mask by using a third sub classification module included in the classification module.

In an alternative embodiment, the determining of the type for the attribute of the suspicious nodule may further include determining a first type for a solid attribute of the suspicious nodule based on the patch and the mask by using a first attribute classification module included in the first sub classification module, determining a second type for the solid attribute of the suspicious nodule based on the patch and the mask by using a second attribute classification module included in the first sub classification module, and finally determining a type for the solid attribute of the suspicious nodule based on a result of comparing the first type and the second type by using a third attribute classification module included in the first sub classification module. In this case, the first attribute classification module may be pre-trained based on a neural network.

In an alternative embodiment, the determining of the second type may include calculating a ratio of voxels in which Hounsfield unit values of voxels included in the mask are higher than a predetermined Hounsfield unit value in the patch by using the second attribute classification module, comparing the ratio of the voxels and a threshold value by using the second attribute classification module, and determining the second type for the solid attribute of the suspicious nodule present in the patch based on a result of the comparison.

In an alternative embodiment, the finally determining of the type for the solid attribute of the suspicious nodule may include when the first type is a type not included in the second type, determining the first type as a final type for the solid attribute of the suspicious nodule by using the third attribute classification module, and when the first type is a type included in the second type, determining the second type as the final type for the solid attribute of the suspicious nodule by using the third attribute classification module.

In an alternative embodiment, the first type may include a solid, a part-solid, or a non-solid. In addition, the second type may include the solid or the non-solid.

In an alternative embodiment, the second sub classification module may be pre-trained based on a neural network.

In an alternative embodiment, the determining of whether the suspicious nodule is calcified may include calculating a ratio of voxels in which Hounsfield unit values of the voxels included in the mask are higher than a predetermined Hounsfield unit value in the patch by using the third sub classification module, comparing the ratio of the voxels and a threshold value by using the third sub classification module, and determining whether the suspicious nodule present in the patch is calcified based on a result of the comparison.

In an alternative embodiment, the third sub classification module may be pre-trained based on a neural network.

In order to realize the object, according to an embodiment of the present disclosure, disclosed is a computer program stored in a computer readable storage medium. When the computer program is executed by one or more processors, the following operations for analyzing a lesion based on a medical image, and the operations may include: an operation of generating, by using a pre-processing module, an input image of a pre-trained detection module from the medical image including a chest region; an operation of generating, by using the detection module, a probability value regarding a presence of a nodule in at least one region of interest and first location information about the at least one region of interest, based on the input image; and an operation of determining, by using a post-processing module, second location information about a suspicious nodule present in the medical image from the first location information, based on the probability value regarding the presence of the nodule.

In order to realize the object, according to an embodiment of the present disclosure, disclosed is a computing device for analyzing a lesion based on a medical image. The device may include: a processor including at least one core; a memory including program codes executable in the processor; and a network unit receiving a medical image including a chest region, in which the processor may generate, by using a pre-processing module, an input image of a pre-trained detection module from the medical image including a chest region, generate, by using the detection module, a probability value regarding a presence of a nodule in at least one region of interest and first location information about the at least one region of interest, based on the input image, and determine, by using a post-processing module, second location information about a suspicious nodule present in the medical image from the first location information, based on the probability value regarding the presence of the nodule.

In order to realize the object, according to an embodiment of the present disclosure, disclosed is a user terminal providing a user interface. The user terminal may include: a processor including at least one core; a memory; a network unit receiving a user interface based on analysis information of a lesion included in a medical image from a computing device; and an output unit providing the user interface. In this case, the analysis information of the lesion may include at least one of location information of a suspicious nodule, a mask for the suspicious nodule, a class of a state of the suspicious nodule, numerical information of the suspicious nodule, measurement information for the suspicious nodule, or malignancy of the suspicious nodule.

According to an embodiment of the present disclosure, a method for detecting and measuring a lesion for diagnosis of a specific disease present in a medical image can be provided.

DETAILED DESCRIPTION

Figure 1:
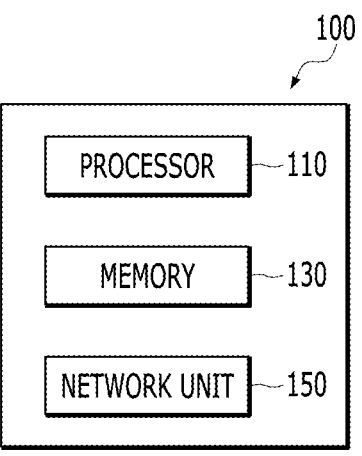
FIG. 1 is a block diagram of a computing device for analyzing a lesion based on a medical image according to an embodiment of the present disclosure.

Various exemplary embodiments will now be described with reference to drawings. In the present specification, various descriptions are presented to provide appreciation of the present disclosure. However, it is apparent that the exemplary embodiments can be executed without the specific description.

"Component", "module", "system", and the like which are terms used in the specification refer to a computer-related entity, hardware, firmware, software, and a combination of the software and the hardware, or execution of the software. For example, the component may be a processing procedure executed on a processor, the processor, an object, an execution thread, a program, and/or a computer, but is not limited thereto. For example, both an application executed in a computing device and the computing device may be the components. One or more components may reside within the processor and/or a thread of execution. One component may be localized in one computer. One component may be distributed between two or more computers. Further, the components may be executed by various computer-readable media having various data structures, which are stored therein. The components may perform communication through local and/or remote processing according to a signal (for example, data transmitted from another system through a network such as the Internet through data and/or a signal from one component that interacts with other components in a local system and a distribution system) having one or more data packets, for example.

The term "or" is intended to mean not exclusive "or" but inclusive "or". That is, when not separately specified or not clear in terms of a context, a sentence "X uses A or B" is intended to mean one of the natural inclusive substitutions. That is, the sentence "X uses A or B" may be applied to any of the case where X uses A, the case where X uses B, or the case where X uses both A and B. Further, it should be understood that the term "and/or" used in this specification designates and includes all available combinations of one or more items among enumerated related items.

It should be appreciated that the term "comprise" and/or "comprising" means presence of corresponding features and/or components. However, it should be appreciated that the term "comprises" and/or "comprising" means that presence or addition of one or more other features, components, and/or a group thereof is not excluded. Further, when not separately specified or it is not clear in terms of the context that a singular form is indicated, it should be construed that the singular form generally means "one or more" in this specification and the claims.

The term "at least one of A or B" should be interpreted to mean "a case including only A", "a case including only B", and "a case in which A and B are combined".

Those skilled in the art need to recognize that various illustrative logical blocks, configurations, modules, circuits, means, logic, and algorithm steps described in connection with the exemplary embodiments disclosed herein may be additionally implemented as electronic hardware, computer software, or combinations of both sides. To clearly illustrate the interchangeability of hardware and software, various illustrative components, blocks, configurations, means, logic, modules, circuits, and steps have been described above generally in terms of their functionalities. Whether the functionalities are implemented as the hardware or software depends on a specific application and design restrictions given to an entire system. Skilled artisans may implement the described functionalities in various ways for each particular application. However, such implementation decisions should not be interpreted as causing a departure from the scope of the present disclosure.

The description of the presented exemplary embodiments is provided so that those skilled in the art of the present disclosure use or implement the present disclosure. Various modifications to the exemplary embodiments will be apparent to those skilled in the art. Generic principles defined herein may be applied to other embodiments without departing from the scope of the present disclosure. Therefore, the present disclosure is not limited to the exemplary embodiments presented herein. The present disclosure should be analyzed within the widest range which is coherent with the principles and new features presented herein.

In the present disclosure, a network function and an artificial neural network and a neural network may be interchangeably used.

Meanwhile, the term "image" or "image data" used throughout the detailed description and claims of the present disclosure refers to multi-dimensional data constituted by discrete image elements (e.g., pixels in a 2D image), and in other words, refers to an object which may be seen with an eye (e.g., displayed on a video screen) or a digital representation of the object (such as a file corresponding to a pixel output of CT, MRI detector, etc.).

For example, the "image" may be computed tomography (CT), magnetic resonance imaging (MRI), ultrasonic waves, a medical image of a subject collected by any other medical imaging system known in the technical field of the present disclosure. The image may not particularly be provided in a medical context, and may be provided in a non-medical context, and may be for example, a security search X-ray imaging.

Throughout the detailed description and claims of the present disclosure, a 'Digital Imaging and Communications in Medicine (DICOM)' standard is a term which collectively refers to several standards used for digital image representation and communication in a medical device, so that the DICOM standard is announced by the Federation Committee, constituted in the American College Radiology (ACR) and the National Electrical Manufacturers Association (NEMA).

Further, throughout the detailed description and claims of the present disclosure, a Picture Archiving and Communication System (PACS)' is a term that refers to a system for performing storing, processing, and transmitting according to the DICOM standard, and medical images acquired by using digital medical image equipment such as X-ray, CT, and MM may be stored in a DICOM format and transmitted to terminals inside or outside a hospital through a network, and additionally include a reading result and a medical chart.

FIG. 1 is a block diagram of a computing device for analyzing a lesion based on a medical image according to an embodiment of the present disclosure.

A configuration of the computing device 100 illustrated in FIG. 1 is only an example shown through simplification. In an exemplary embodiment of the present disclosure, the computing device 100 may include other components for performing a computing environment of the computing device 100 and only some of the disclosed components may constitute the computing device 100.

The computing device 100 may include a processor 110, a memory 130, and a network unit 150.

The processor 110 may be constituted by one or more cores and may include processors for data analysis and deep learning, which include a central processing unit (CPU), a general purpose graphics processing unit (GPGPU), a tensor processing unit (TPU), and the like of the computing device. The processor 110 may read a computer program stored in the memory 130 to perform data processing for machine learning according to an exemplary embodiment of the present disclosure.

According to an exemplary embodiment of the present disclosure, the processor 110 may perform a calculation for learning the neural network. The processor 110 may perform calculations for learning the neural network, which include processing of input data for learning in deep learning (DL), extracting a feature in the input data, calculating an error, updating a weight of the neural network using backpropagation, and the like. At least one of the CPU, GPGPU, and TPU of the processor 110 may process learning of a network function. For example, both the CPU and the GPGPU may process the learning of the network function and data classification using the network function. Further, in an exemplary embodiment of the present disclosure, processors of a plurality of computing devices may be used together to process the learning of the network function and the data classification using the network function. Further, the computer program executed in the computing device according to an exemplary embodiment of the present disclosure may be a CPU, GPGPU, or TPU executable program.

According to an embodiment of the present disclosure, the processor 110 may read a lesion related to a specific disease based on a medical image using at least one pre-trained machine learning module. The processor 110 inputs the medical image to a first machine learning module to identify location information of a lesion present in the medical image. The processor 110 may generate a patch corresponding to a portion of the medical image based on the location information of the lesion. The processor 110 may generate a mask for the lesion by inputting the patch corresponding to the location information of the lesion to a second machine learning module. In this case, the mask may mean a data aggregate including information about a region in which the lesion present in the medical image. The processor 110 inputs the patch and the mask into a third machine learning module to generate class information representing a state of the lesion. Through such an operation, the processor 110 may generate information (e.g., a location, a state, etc., of the lesion in the body, etc.) on a lesion which becomes a diagnosis criterion of the specific disease based on the medical image.

For example, the processor 110 may input a medical image including a chest region input into the network unit 150 to a pre-trained search module. In this case, the medical image including the chest region may include a 3D CT image including at least one lung tissue. The processor 110 may obtain location information of a suspicious nodule present in the medical image by inputting the medical image including the chest region into the search module. The location information of the suspicious nodule may include a center coordinate system of a region in the medical image identified as the suspicious nodule. When the medical image is the 3D CT image, the location information of the suspicious nodule may include (X, Y, Z) coordinate values of the center of the region determined as the suspicious nodule.

The processor 110 may extract the patch corresponding to the location information from the medical image including the chest region based on the location information of the suspicious nodule obtained by using the search module. The processor 110 may input the patch corresponding to the location information of the suspicious nodule to a pre-trained measurement module. The processor 110 may generate a mask for the suspicious nodule by inputting the patch generated from the medical image into the measurement module. In other words, the processor 110 may extract information on the region in which the suspicious nodule is present in the patch by using the measurement module.

The processor 110 may input the previously extracted patch together with the mask for the suspicious nodule generated using the measurement module into a pre-trained classification module. The processor 110 may classify a class related to the state of the suspicious nodule by inputting the mask and the patch for the suspicious nodule together into the classification module. At this time, the state of the suspicious nodule may include features, attributes, etc., of the suspicious nodule, which are the basis for determining the lung disease. In other words, the processor 110 may identify the state of the suspicious nodule in the patch of the medical image by using the classification module in order to obtain lesion information for diagnosing the lung disease.

According to an embodiment of the present disclosure, the processor 110 may measure the lesion read from the medical image based on an auxiliary index for diagnosing the specific disease. The processor 110 may calculate numerical values for the region where the lesion is present based on the mask generated through a second machine learning module. The processor 110 may calculate an assessment score of the lesion based on numerical information including the numerical values of the lesion and the class information for the state of the lesion, based on the auxiliary index for diagnosing the specific disease. Further, the processor 110 may predict the malignancy of the lesion using the pre-trained machine learning module. The processor 110 may estimate the malignancy of the lesion based on the location information of the lesion, the class information for the state of the lesion, and the numerical information of the lesion through a fourth machine learning module. Through such an operation, the processor 110 may generate measurement information on the lesion that may be used as a diagnostic index for the specific disease based on the medical image.

For example, the processor 110 may generate the numerical information for the region in which the suspicious nodule is present in the medical image based on the mask of the suspicious nodule generated using the measurement module. In this case, the numerical information may include numerical values related to a diameter and a volume of the suspicious nodule. The processor 110 calculates the assessment score of the suspicious nodule according to the auxiliary index of lung disease diagnosis stored in the memory 130 based on the numerical information of the suspicious nodule and the class of the state of the suspicious nodule classified using the classification module. At this time, the auxiliary index of the lung disease diagnosis may include a classification index based on Lung CT Screening Reporting and Data System (Lung-RADS). In other words, the processor 110 may determine the assessment score of the suspicious nodule according to a criterion determined according to the auxiliary index for the lung disease diagnosis by using structural information and attribute information of the suspicious nodule together. The assessment score determined by the processor 110 may be used for diagnosing a lung disease and predicting a prognosis of a subject in the medical image.

The processor 110 may input the location information of the suspicious nodule generated through the search module, the class information for the state of the suspicious nodule generated through the classification module, and the numeric information of the suspicious nodule generated based on the mask into a pre-trained malignancy prediction module. The processor 110 may estimate the malignancy of the suspicious nodule by inputting the location information, the class information, and the numerical information of the suspicious nodule into the malignancy prediction module. In addition, the processor 110 may estimate the malignancy of the suspicious nodule by inputting the patch extracted from the medical image and the mask generated through the measurement module into the malignancy prediction module. In other words, the processor 110 may estimate the malignancy of the suspicious nodule using quantitative information for the suspicious nodule itself, or may estimate the malignancy of the suspicious nodule using image information for the suspicious nodule. The processor 110 may predict the malignancy of the suspicious nodule affecting the lung disease by considering the location information, the structural information, and the attribute information of the suspicious nodule present in the medical image including the chest region together through the malignancy prediction module. The malignancy predicted by the processor 110 may be used for diagnosing the lung disease and predicting a prognosis for the subject in the medical image.

According to an embodiment of the present disclosure, the processor 110 may modify the assessment score for the lesion based on medical images of a specific subject having a time-series relationship using the pre-trained machine learning module. When a medical image of the same subject as the image pre-analyzed by the processor 110 is input to the computing device 100, the processor 110 may determine changed information by matching lesions which are present in the pre-analyzed image and a subsequently input medical image by using a fifth machine learning module. In addition, the processor 110 may modify the assessment score by reflecting the changed information to the assessment score for the lesion. If there is no changed information, the processor 110 may maintain the assessment score for the lesion as it is without separate modification.

For example, the processor 110 may perform the above-described operations for calculating the assessment score of the suspicious nodule based on the medical image received through the network unit 150 and store the assessment score in the memory 130. When a new medical image is received through the network unit 150, the processor 110 may determine whether the subject of the new medical image corresponds to the subject of the pre-analyzed medical images. In other words, the processor 110 may check whether an ID for identifying the subject of the new medical image matches one of IDs of the pre-analyzed medical images. If the identification ID of the new medical image matches one of the identification IDs of the pre-analyzed medical images, the processor 110 may match the same suspicious nodule which is present in the existing image and the new image by using a pre-trained tracking module. The processor 110 may identify changed information of the matched suspicious nodule using the tracking module, and modify the assessment score for the suspicious nodule based on the changed information. Through such an operation, the processor 110 may effectively track changes in the lesion of a specific subject and increase the accuracy of information necessary for determining the prognosis of the lung disease.

According to an exemplary embodiment of the present disclosure, the memory 130 may store any type of information generated or determined by the processor 110 and any type of information received by the network unit 150.

According to an exemplary embodiment of the present disclosure, the memory 130 may include at least one type of storage medium of a flash memory type storage medium, a hard disk type storage medium, a multimedia card micro type storage medium, a card type memory (for example, an SD or XD memory, or the like), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk. The computing device 100 may operate in connection with a web storage performing a storing function of the memory 130 on the Internet. The description of the memory is just an example and the present disclosure is not limited thereto.

The network unit 150 according to several embodiments of the present disclosure may use various wired communication systems, such as a Public Switched Telephone Network (PSTN), an x Digital Subscriber Line (xDSL), a Rate Adaptive DSL (RADSL), a Multi Rate DSL (MDSL), a Very High Speed DSL (VDSL), a Universal Asymmetric DSL (UADSL), a High Bit Rate DSL (HDSL), and a local area network (LAN).

The network unit 150 presented in the present specification may use various wireless communication systems, such as Code Division Multi Access (CDMA), Time Division Multi Access (TDMA), Frequency Division Multi Access (FDMA), Orthogonal Frequency Division Multi Access (OFDMA), Single Carrier-FDMA (SC-FDMA), and other systems.

In the present disclosure, the network unit 150 may be configured regardless of a communication aspect, such as wired communication and wireless communication, and may be configured by various communication networks, such as a Personal Area Network (PAN) and a Wide Area Network (WAN). Further, the network may be a publicly known World Wide Web (WWW), and may also use a wireless transmission technology used in short range communication, such as Infrared Data Association (IrDA) or Bluetooth.

The network unit 150 according to an exemplary embodiment of the present disclosure may use an arbitrary type known wired/wireless communication systems.

The network unit 150 may receive a medical image in which a body organ is expressed from a medical image capturing system. For example, the medical image in which the body organ is expressed may be training data or inference data of the machine learning module learned as a 2D feature or a 3D feature. The medical image in which the body organ is expressed may be a 3D CT region including at least one lung region. The medical image in which the body organ is expressed is not limited to the above-described example, and may include all images related to the body organ obtained through capturing, such as an X-ray image, an MR image, etc.

In addition, the network unit 150 may transmit and receive information processed by the processor 110, a user interface, and the like through communication with other terminals. For example, the network unit 150 may provide the user interface generated by the processor 110 to a client (e.g., a user terminal). In addition, the network unit 150 may receive an external input of a user applied to a client and transfer the external input to the processor 110. In this case, the processor 110 may process operations such as outputting, correcting, changing, adding, and the like of information provided through the user interface based on the external input of the user received from the network unit 150.

Meanwhile, according to an embodiment of the present disclosure, the computing device 100 may include a server as a computing system that transmits and receives information through communication with the client. In this case, the client may be any type of terminal which may access the server. For example, the computing device 100 as the server may receive the medical image from the medical image capturing system and analyze the lesion, and provide a user interface including an analysis result to the user terminal. At this time, the user terminal may output the user interface received from the computing device 100 as the server, and receive or process information through interaction with the user.

The user terminal may display the user interface provided to provide analysis information of the lesion (e.g., suspicious nodule) included in the medical image transmitted from the computing device 100 as the server. Although not separately illustrated, the user terminal may include a network unit receiving the user interface from the computing device 100, a processor including at least one core, a memory, an output unit providing the user interface, and input unit receiving the external input applied from the user.

In an additional embodiment, the computing device 100 may also include any type of terminal that receives data resources generated by an arbitrary server and performs additional information processing.

Figure 2:
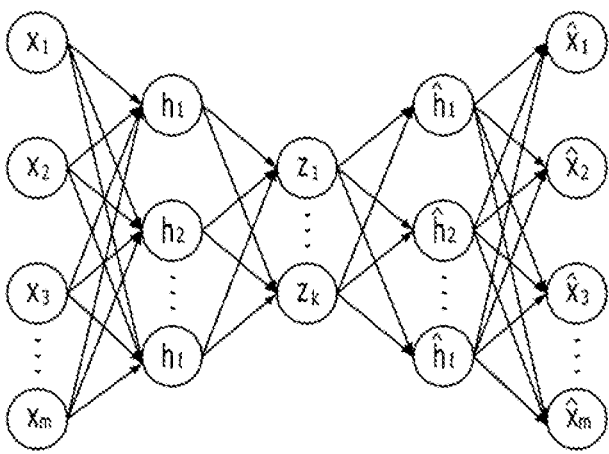
FIG. 2 is a schematic view illustrating a network function according to an embodiment of the present disclosure.

FIG. 2 is a schematic diagram illustrating a network function according to an exemplary embodiment of the present disclosure.

Throughout the present specification, a computation model, the neural network, a network function, and the neural network may be used as the same meaning. The neural network may be generally constituted by an aggregate of calculation units which are mutually connected to each other, which may be called nodes. The nodes may also be called neurons. The neural network is configured to include one or more nodes. The nodes (alternatively, neurons) constituting the neural networks may be connected to each other by one or more links.

In the neural network, one or more nodes connected through the link may relatively form the relationship between an input node and an output node. Concepts of the input node and the output node are relative and a predetermined node which has the output node relationship with respect to one node may have the input node relationship in the relationship with another node and vice versa.

As described above, the relationship of the input node to the output node may be generated based on the link. One or more output nodes may be connected to one input node through the link and vice versa.

In the relationship of the input node and the output node connected through one link, a value of data of the output node may be determined based on data input in the input node. Here, a link connecting the input node and the output node to each other may have a weight. The weight may be variable and the weight is variable by a user or an algorithm in order for the neural network to perform a desired function. For example, when one or more input nodes are mutually connected to one output node by the respective links, the output node may determine an output node value based on values input in the input nodes connected with the output node and the weights set in the links corresponding to the respective input nodes.

As described above, in the neural network, one or more nodes are connected to each other through one or more links to form a relationship of the input node and output node in the neural network. A characteristic of the neural network may be determined according to the number of nodes, the number of links, correlations between the nodes and the links, and values of the weights granted to the respective links in the neural network. For example, when the same number of nodes and links exist and there are two neural networks in which the weight values of the links are different from each other, it may be recognized that two neural networks are different from each other.

The neural network may be constituted by a set of one or more nodes. A subset of the nodes constituting the neural network may constitute a layer. Some of the nodes constituting the neural network may constitute one layer based on the distances from the initial input node. For example, a set of nodes of which distance from the initial input node is n may constitute n layers. The distance from the initial input node may be defined by the minimum number of links which should be passed through for reaching the corresponding node from the initial input node. However, a definition of the layer is predetermined for description and the order of the layer in the neural network may be defined by a method different from the aforementioned method. For example, the layers of the nodes may be defined by the distance from a final output node.

The initial input node may mean one or more nodes in which data is directly input without passing through the links in the relationships with other nodes among the nodes in the neural network. Alternatively, in the neural network, in the relationship between the nodes based on the link, the initial input node may mean nodes which do not have other input nodes connected through the links. Similarly thereto, the final output node may mean one or more nodes which do not have the output node in the relationship with other nodes among the nodes in the neural network. Further, a hidden node may mean nodes constituting the neural network other than the initial input node and the final output node.

In the neural network according to an exemplary embodiment of the present disclosure, the number of nodes of the input layer may be the same as the number of nodes of the output layer, and the neural network may be a neural network of a type in which the number of nodes decreases and then, increases again from the input layer to the hidden layer. Further, in the neural network according to another exemplary embodiment of the present disclosure, the number of nodes of the input layer may be smaller than the number of nodes of the output layer, and the neural network may be a neural network of a type in which the number of nodes decreases from the input layer to the hidden layer. Further, in the neural network according to yet another exemplary embodiment of the present disclosure, the number of nodes of the input layer may be larger than the number of nodes of the output layer, and the neural network may be a neural network of a type in which the number of nodes increases from the input layer to the hidden layer. The neural network according to still yet another exemplary embodiment of the present disclosure may be a neural network of a type in which the neural networks are combined.

A deep neural network (DNN) may refer to a neural network that includes a plurality of hidden layers in addition to the input and output layers. When the deep neural network is used, the latent structures of data may be determined. That is, latent structures of photos, text, video, voice, and music (e.g., what objects are in the photo, what the content and feelings of the text are, what the content and feelings of the voice are) may be determined. The deep neural network may include a convolutional neural network (CNN), a recurrent neural network (RNN), an auto encoder, generative adversarial networks (GAN), a restricted Boltzmann machine (RBM), a deep belief network (DBN), a Q network, a U network, a Siam network, a Generative Adversarial Network (GAN), and the like.

The description of the deep neural network described above is just an example and the present disclosure is not limited thereto.

In an exemplary embodiment of the present disclosure, the network function may include the auto encoder. The auto encoder may be a kind of artificial neural network for outputting output data similar to input data. The auto encoder may include at least one hidden layer and odd hidden layers may be disposed between the input and output layers. The number of nodes in each layer may be reduced from the number of nodes in the input layer to an intermediate layer called a bottleneck layer (encoding), and then expanded symmetrical to reduction to the output layer (symmetrical to the input layer) in the bottleneck layer. The auto encoder may perform non-linear dimensional reduction. The number of input and output layers may correspond to a dimension after preprocessing the input data. The auto encoder structure may have a structure in which the number of nodes in the hidden layer included in the encoder decreases as a distance from the input layer increases. When the number of nodes in the bottleneck layer (a layer having a smallest number of nodes positioned between an encoder and a decoder) is too small, a sufficient amount of information may not be delivered, and as a result, the number of nodes in the bottleneck layer may be maintained to be a specific number or more (e.g., half of the input layers or more).

The neural network may be learned in at least one scheme of supervised learning, unsupervised learning, semi supervised learning, or reinforcement learning. The learning of the neural network may be a process in which the neural network applies knowledge for performing a specific operation to the neural network.

The neural network may be learned in a direction to minimize errors of an output. The learning of the neural network is a process of repeatedly inputting training data into the neural network and calculating the output of the neural network for the training data and the error of a target and back-propagating the errors of the neural network from the output layer of the neural network toward the input layer in a direction to reduce the errors to update the weight of each node of the neural network. In the case of the supervised learning, the training data labeled with a correct answer is used for each training data (i.e., the labeled training data) and in the case of the unsupervised learning, the correct answer may not be labeled in each training data. That is, for example, the training data in the case of the supervised learning related to the data classification may be data in which category is labeled in each training data. The labeled training data is input to the neural network, and the error may be calculated by comparing the output (category) of the neural network with the label of the training data. As another example, in the case of the unsupervised learning related to the data classification, the training data as the input is compared with the output of the neural network to calculate the error. The calculated error is back-propagated in a reverse direction (i.e., a direction from the output layer toward the input layer) in the neural network and connection weights of respective nodes of each layer of the neural network may be updated according to the back propagation. A variation amount of the updated connection weight of each node may be determined according to a learning rate.

Calculation of the neural network for the input data and the back-propagation of the error may constitute a learning cycle (epoch). The learning rate may be applied differently according to the number of repetition times of the learning cycle of the neural network. For example, in an initial stage of the learning of the neural network, the neural network ensures a certain level of performance quickly by using a high learning rate, thereby increasing efficiency and uses a low learning rate in a latter stage of the learning, thereby increasing accuracy.

In learning of the neural network, the training data may be generally a subset of actual data (i.e., data to be processed using the learned neural network), and as a result, there may be a learning cycle in which errors for the training data decrease, but the errors for the actual data increase. Overfitting is a phenomenon in which the errors for the actual data increase due to excessive learning of the training data. For example, a phenomenon in which the neural network that learns a cat by showing a yellow cat sees a cat other than the yellow cat and does not recognize the corresponding cat as the cat may be a kind of overfitting. The overfitting may act as a cause which increases the error of the machine learning algorithm. Various optimization methods may be used in order to prevent the overfitting. In order to prevent the overfitting, a method such as increasing the training data, regularization, dropout of omitting a part of the node of the network in the process of learning, utilization of a batch normalization layer, etc., may be applied.

Figure 3:
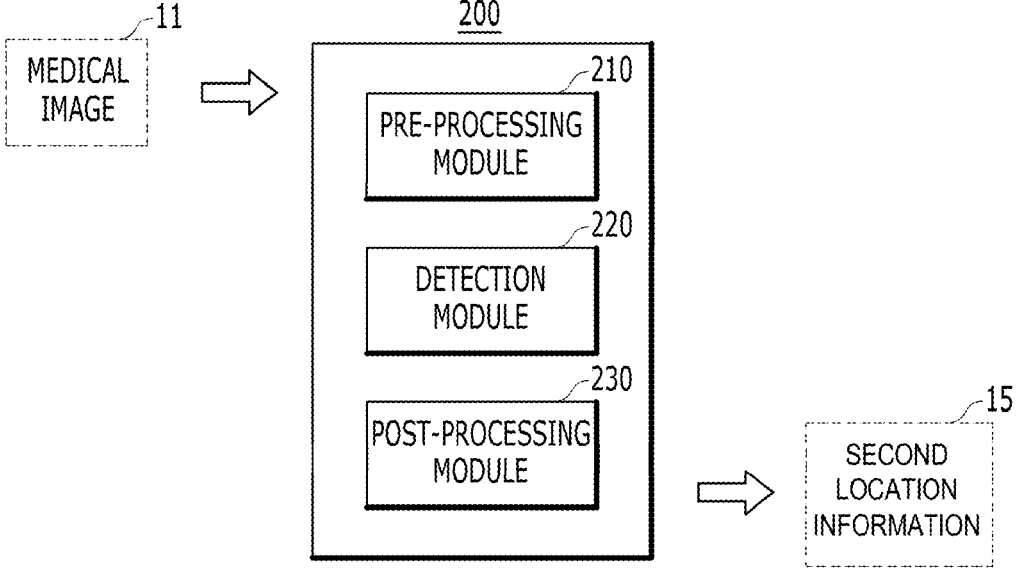
FIG. 3 is a block diagram illustrating an operation process of a search module included in the computing device according to an embodiment of the present disclosure.
Figure 4:
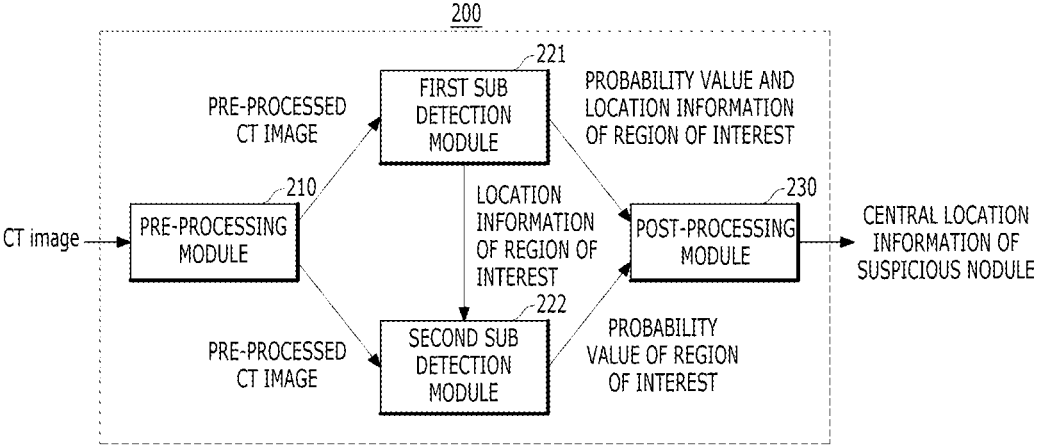
FIG. 4 is a block diagram illustrating a structure of the search module according to an embodiment of the present disclosure.

FIGS. 3 and 4 are block diagrams illustrating an operation process and a structure of a detection module included in the computing device according to an embodiment of the present disclosure.

Referring to FIG. 3, the computing device 100 according to an embodiment of the present disclosure may include a search module 200 that extracts information about a suspicious nodule present in a medical image 11. The search module 200 may include a pre-processing module 210 that generates an input image of a detection module 220 from the medical image 11 including a chest region transmitted to the computing device 100, a detection module 220 that derives information on at least one region of interest based on the input image generated through the pre-processing module 210, and a post-processing module 230 that derives location information for the suspicious nodule based on the information on the region of interest derived through the detection module 220. In this case, the detection module 220 included in the search module 200 may include at least one neural network. The detection module 220 may perform the above-described operations through a pre-trained neural network. The pre-processing module 210 and the post-processing module 230 may also include at least one pre-trained neural network, and may perform the above-described operations through the neural network.

Referring to FIG. 4, the pre-processing module 210 may receive a CT image of capturing lung tissue, which is a 3D medical image including the chest region, as an input. The pre-processing module 210 may classify the input CT image into image group units based on a standard DICOM format. At this time, a classifier generally adopts a value suggesting the same series among type-1 attributes of DICOM, but may actually depend on an environment used by the computing device 100. As described above, the pre-processing module 210 may classify the CT images into image group units by itself or may receive already classified CT images as the input.

The pre-processing module 210 may calculate a Hounsfield unit (HU) value based on the image group classified by the classifier. For example, the pre-processing module 210 may sequentially calculate Hounsfield unit values from image groups using attribute values based on the standard DICOM format. At this time, the attribute values based on the standard DICOM format may be Rescale Intercept Attribute (0028, 1052) and Rescale Slope Attribute (0028, 1053). The pre-processing module 210 may not use the calculated Hounsfield unit value as it is, and cut the Hounsfield unit value to a first range such as [−1000, 600], and then linearly transform the first range into a second range such as [0, 1]. Subsequently, the pre-processing module 210 performs interpolation such as cubic B-spline interpolation to transform the image so that voxel spacing for each of three axes: axial, coronal, and sagittal satisfies a predetermined numerical value. For example, the predetermined numerical values may be 1.0, 0.67, 0.67 for respective axes. However, the above numerical values and descriptions are only examples, and are not limitedly interpreted, and can be changed within a scope that can be understood by those skilled in the art. The pre-processing module 210 may generate 2D images from the CT image in which the Hounsfield unit value is calculated. That is, since the detection module 220 includes a 2.5-dimensional neural network module that uses the 2-dimensional image as the input, the pre-processing module 210 may perform a task of processing of the image into a form suitable for the input of the detection module 220. For example, the detection module 220 may include the 2.5-dimensional neural network module using an input of (axial, coronal, sagittal)=(7, 540, 540). However, the above numerical values and descriptions are only examples, and are not limitedly interpreted, and can be changed within a scope that can be understood by those skilled in the art. According to an input size of the 2.5 D neural network module, the pre-processing module 210 may generate the 2D images by processing the 3D CT image. The 2D images generated by the pre-processing module 210 may be used as an input of a first sub detection module 221 of the detection module 220 to be described below.

Referring to FIG. 4, the detection module 220 may include the first sub detection module 221 that generates a first probability value and first location information for at least one ROI based on the input image generated through the pre-processing module 210 and a second sub detection module 222 that estimates a second probability value for at least one ROI based on the input image generated through the pre-processing module 210 and the first location information. In this case, the first probability value and the second probability value may be numerical values representing probabilities that respective ROIs identified by the respective modules 221 and 222 will include the suspicious nodule. For example, the CT image passing through the pre-processing module 210 may input into the first sub detection module 221 and the second sub detection module 222, respectively, and be used for extracting information on the ROIs determined to include the nodule. The first sub detection module 221 may receive the pre-processed CT image as the input and calculate the first probability value and a coordinate value for at least one ROI. In this case, the coordinate value calculated by the first sub detection module 221 may be used as the input of the second sub detection module 222. The second sub detection module 222 may extract a 3D patch from the pre-processed CT image based on the coordinate value calculated by the first sub detection module 221. The second sub detection module 222 may again estimate a second probability value in which the region of interest identified by the first sub detection module 221 will include an actual nodule based on the 3D patch.

Detailed operation processes and structures of the first sub detection module 221 and the second sub detection module 222 will be described later in detail with reference to FIGS. 5 and 6.

The post-processing module 230 may derive information on the suspicious nodule, which is a final output value of the search module 200, based on the information on the region of interest derived through the detection module 220. The post-processing module 230 may generate a third probability value for a presence of a nodule through a weighted sum of the first probability value derived through the first sub detection module 221 and the second probability value derived through the second sub detection module 222. The post-processing module 230 may select a region corresponding to the suspicious nodule among the regions of interest by comparing the third probability value and a threshold value. In other words, the post-processing module 230 may determine location information of the region of interest corresponding to the probability value selected as a result of comparison between the third probability value and the threshold value as the location information of the suspicious nodule. Through the above-described process, the post-processing module 230 may finally output second location information 15 including a central coordinate value of the suspicious nodule.

For example, it is assumed that the first probability value of the first sub detection module 221 is $p_1$, the second probability value of the second sub detection module 222 is $p_2$, and a diameter of the ROI identified by the first sub detection module 221 is d. The post-processing module 230 may determine the third probability value p for each ROI in the following scheme using three input values described above.

(1) When $p_1 < 0.05$, p=0.
(2) When $d \geq 7$ [mm], $p_1 < 0.97$, p=0.
(3) When $d \leq 4$ [mm], $p_1 < 0.97$, p=0.
(4) Otherwise, $p = 0.2 \times p_1 + 0.8 \times p_2$.

When the third probability value p is equal to or more than a predetermined threshold value, the post-processing module 230 may set the central coordinate value of the region of interest corresponding to a probability value equal to or more than the threshold value as a final output. A default value of the predetermined threshold value may be 0.82, and may be changed to 0.78 or 0.91 according to sensitivity. However, the above numerical values and descriptions are only examples, and are not limitedly interpreted, and can be changed within a scope that can be understood by those skilled in the art.

Figure 5:
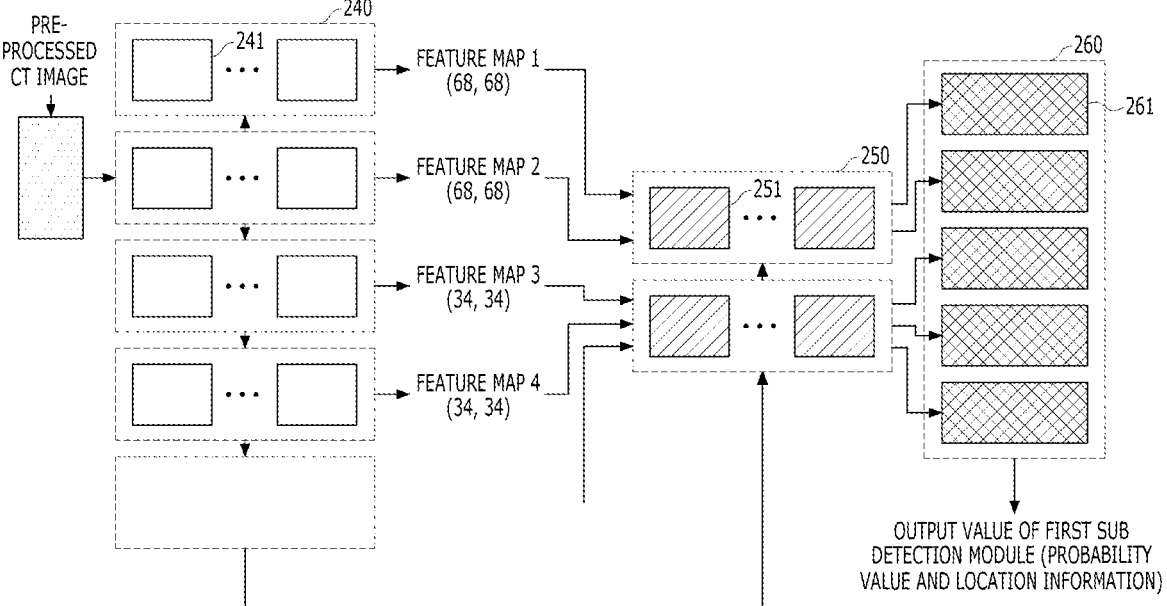
FIG. 5 is a block diagram illustrating a structure of a first sub detection module included in the search module according to an embodiment of the present disclosure.

FIG. 5 is a block diagram illustrating a structure of a first sub detection module included in the search module according to an embodiment of the present disclosure.

Referring to FIG. 5, the first sub detection module 221 according to an embodiment of the present disclosure may include a first neural network module 240 that receives the 2D images generated by the pre-processing module 210 as the input and generates first feature maps having various sizes. The first sub detection module 221 may include a second neural network module 250 that generates second feature maps by concatenating at least some of the first feature maps based on the sizes of the first feature maps. In addition, the first sub detection module 221 may include a third neural network module 260 that generates the first probability value and the first location information for at least one ROI by matching the second feature maps with a predetermined anchor box.

For example, the first sub detection module 221 may have a neural network structure that receives the 2.5-dimensional image as the input. As described above, the first sub detection module 221 may receive an image having a form of [7, 540, 540] as the input, and output probability values and coordinate values for a series of regions of interest that are determined to include nodules. Referring to FIG. 5, the neural network of the first sub detection module 221 may have a backbone-neck-head structure.

A backbone structure may include a first neural network module 240 in which a bottleneck block 241 including skip-connection is repeated after a stem-cell block including a pooling layer. The bottleneck block 241 may enlarge or reduce the size of the feature map through a stride value. In the backbone structure, each of the first neural network modules 240 may generate first feature maps having a plurality of sizes for detecting nodules having different sizes. Specifically, the first feature maps having sizes of [68, 68], [68, 68], [34, 34], [34, 34], and [34, 34] may be output values of the first neural network module 240. The first feature maps generated through the first neural network module 240 may be used as an input of a neck structure. However, the above-described size related numerical values are only examples, and are not limitedly interpreted, and can be changed within a scope that can be understood by those skilled in the art.

When it is assumed that a series of processes of generating the output value in the backbone structure are processes of encoding the feature map, the neck structure may be interpreted as a process of decoding the feature map in a form suitable for performing a final detection process by appropriately combining the feature maps generated in the backbone structure. The neck structure may include a second neural network module 250 generating the second feature maps by combining the first feature maps generated by the first neural network module 240 of the backbone structure for each size. The second neural network module 250 may include at least one intermediate block 251 generating second feature maps of the next level by combining first feature maps of adjacent sizes with each other. In addition, the second neural network module 250 may generate the second feature maps by combining all first feature maps given as the input through at least one intermediate block 251. Specifically, one of the second neural network modules 250 may generate the second feature maps by combining first feature maps having sizes corresponding to [68, 68]. Specifically, the other one of the second neural network modules 250 may generate the second feature maps by combining first feature maps having sizes corresponding to [34, 34]. Further, the second neural network module 250 may generate the second feature maps by combining all of the first feature maps. The second feature maps generated through the second neural network module 250 may be used as an input of a head structure.

The head structure may include a third neural network module 260 including detection blocks 261 that individually receive the second feature maps generated through the second neural network module 250 of the neck structure as the input. That is, in the head structure, the third neural network module 260 may generate a probability value for a presence of a nodule value and location information in the ROI corresponding to the output value of the first sub detection module 221 based on the output of the second neural network module 250. Specifically, the detection block 261 of the third neural network module 260 may match the second feature map with a predefined anchor box and output a probability value that the ROI corresponding to the second feature map will include the nodule, and a size and location information of a nodule which is present in an ROI corresponding to an offset between an actual output value and the anchor box.

On the other hand, although not illustrated in FIG. 5, when there are a plurality of regions of interest identified through the third neural network module 260, the first sub detection module 221 may perform a task of clustering regions of interest determined to include the same nodule and integrating the clustered ROIs into one nodule. In addition, the first sub detection module 221 may perform a correction task for first location information of the ROIs through the third neural network module 260. For example, the first sub detection module 221 may cluster at least some of the ROIs based on a ratio of overlapping regions between the ROIs by projecting arbitrary ROIs to the same plane. Specifically, the first sub detection module 221 may calculate an intersection over union (IOU) between arbitrary ROIs, and if the calculated value exceeds a threshold value inversely proportional to a Euclidean distance between the ROIs, the first sub detection module 221 may determine that the ROIs include the same nodule and cluster the ROIs. In the case of the clustered ROIs, the first sub detection module 221 may calculate location information and a diameter value of a region having the highest probability value for a presence of a nodule as representative values. The first sub detection module 221 may finally generate an input value of the second sub detection module 222 by converting the first location information of the ROIs obtained through various inputs into the same coordinate system.

Figure 6:
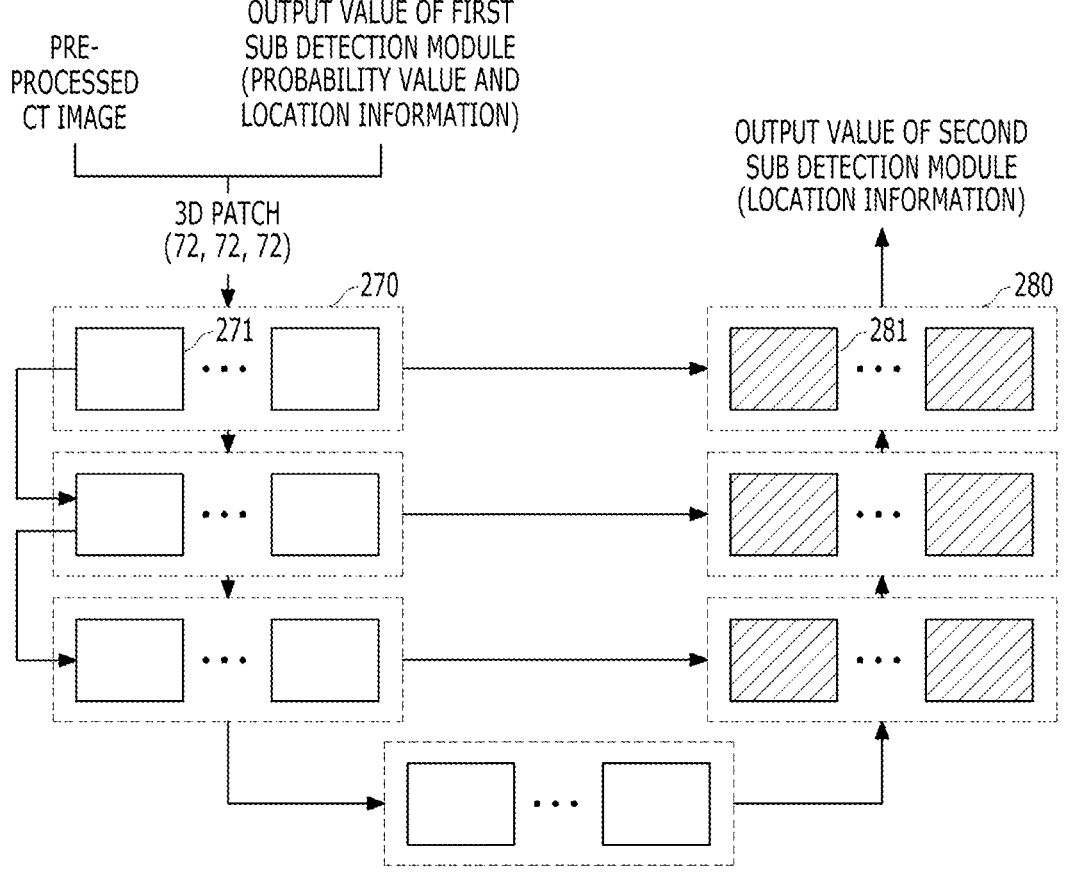
FIG. 6 is a block diagram illustrating a structure of a second sub detection module included in the search module according to an embodiment of the present disclosure.

FIG. 6 is a block diagram illustrating a structure of a second sub detection module included in the search module according to an embodiment of the present disclosure.

Referring to FIG. 6, the second sub detection module 222 according to an embodiment of the present disclosure may include a fourth neural network module 270 generating at least one third feature map by performing encoding based on the 3D patch extracted from an image output by the pre-processing module 210 based on the first location information. At this time, the second sub detection module 222 may extract a region corresponding to the first location information from the preprocessed 3D image as a patch having a predetermined size in order to generate an input patch of the fourth neural network module 270. The second sub detection module 222 may include a fifth neural network module 280 generating at least one fourth feature map by performing decoding based on the third feature map. In addition, although not illustrated in FIG. 6, the second sub detection module 222 may include a sixth neural network module generating a second probability value for at least one ROI based on the feature map generated by integrating the third feature map and the fourth feature map.

For example, the second sub detection module 222 has, as the input value, the 3D patch extracted from the image processed by the pre-processing module 210 using the central coordinate value of the ROI given as the output value of the first sub detection module 221. Specifically, the size of the 3D patch may be [72, 72, 72]. The second sub detection module 222 may receive the 3D patch and output one real value indicating whether the corresponding patch includes the nodule. The second sub detection module 222 may include a neural network having an encoder-decoder structure as illustrated in FIG. 6. The second sub detection module 222 may include a fourth neural network module 270 including one or more encoder blocks 271 for adjusting the size of the 3D patch and a fifth neural network module 280 including one or more decoder blocks 281. The 3D patch passing through the fourth neural network module 270 may be compressed up to a size of [3, 3, 3]. The compressed patch may be restored up to a size of [18, 18, 18] while passing through the fifth neural network module 280. In this restoration process, a combination (element-wise sum) with the third feature map of the fourth neural network module 270 having the same size is performed, and a more complex fourth feature map may be generated. The second sub detection module 222 may output a second probability value regarding the presence of the nodule in the ROI based on the fourth feature map using a sixth neural network module that performs 3D convolution.

On the other hand, the second sub detection module 222 may be trained by performing a first operation of training the neural network based on a randomly sampled training image and a second operation of training the neural network based on a learning image selected based on recall and precision. For example, the second sub detection module 222 may receive randomly sampled 3D patches for training and primarily train the neural network with a 3D feature. When training is completed based on the randomly sampled 3D patches for training, the second sub detection module 222 may secondarily train the neural network based on the 3D patches for training, which are relatively difficult to predict compared to the 3D patches for primarily training. In this case, the 3D patches for training, which are relatively difficult to predict, may be 3D patches with higher recall and lower precision than the 3D patches for primary training. Performance of estimating probability value of the second sub detection module 222 may be greatly enhanced through such a kind of curriculum training.

Figure 7:
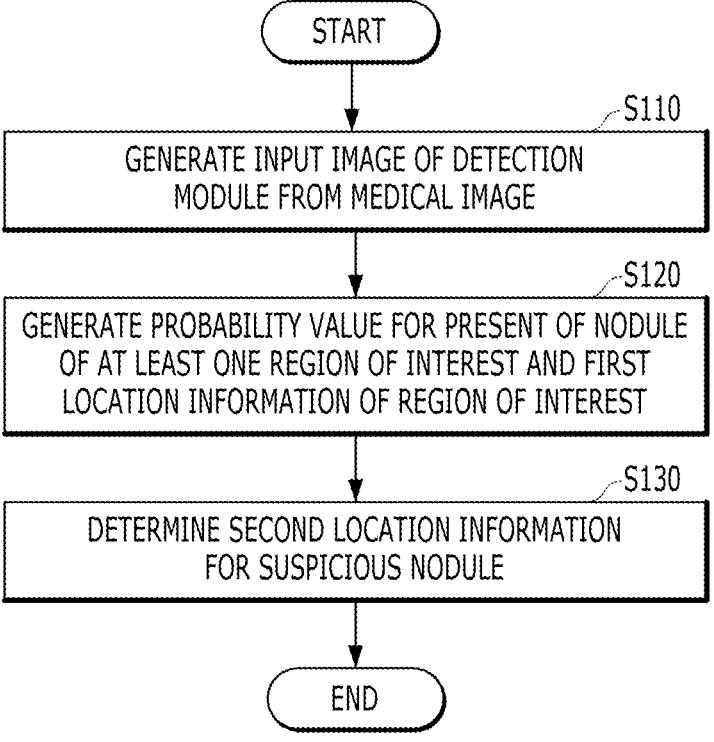
FIG. 7 is a flowchart illustrating the operation process of the search module according to an embodiment of the present disclosure.

FIG. 7 is a flowchart illustrating the operation process of the search module according to an embodiment of the present disclosure.

Referring to FIG. 7, in step S110, a computing device 100 according to an embodiment of the present disclosure may receive a medical image for lesion analysis from a medical image storage and transmission system. The medical image for lesion analysis may be a 3D CT image including a chest region. When the computing device 100 receives the 3D CT image as the medical image, the computing device 100 processes the medical image using a pre-processing module to generate an input image for the detection module. In this case, the pre-processing module may perform extraction of a Hounsfield unit value from the medical image, adjustment of the size through linear transformation and padding of the medical image, and 2D image generation through segmentation of the medical image.

In step S120, the computing device 100 may generate a probability value for the presence of the nodule in at least one ROI and first location information of the ROI based on the image processed through the pre-processing module by using the detection module. In this case, the ROI may be understood as a region in which the nodule is predicted to be present. Therefore, the first location information of the ROI may be understood as a candidate group of location information for a suspicious nodule to be finally determined in step S130 to be described later.

In step S130, the computing device 100 may determine second location information for the suspicious nodule present in the medical image based on the output value of the detection module by using the post-processing module. The computing device 100 may determine the second location information for the suspicious nodule present in the medical image from the first location information based on a probability value for the presence of the nodule by using the post-processing module. For example, when there is a plurality of ROIs, the computing device 100 may compare probability values of the ROIs with a predefined threshold value. The computing device 100 may determine an ROI corresponding to a probability value equal to or more than the predefined threshold value as the suspicious nodule. In other words, the computing device 100 may determine location information (i.e., the first location information) of the ROI corresponding to the probability value equal to or more than the threshold value as the location information (i.e., the second location information) for the suspicious nodule. Through such a process, the computing device 100 may accurately detect the nodule present in the medical image.

Figure 8:
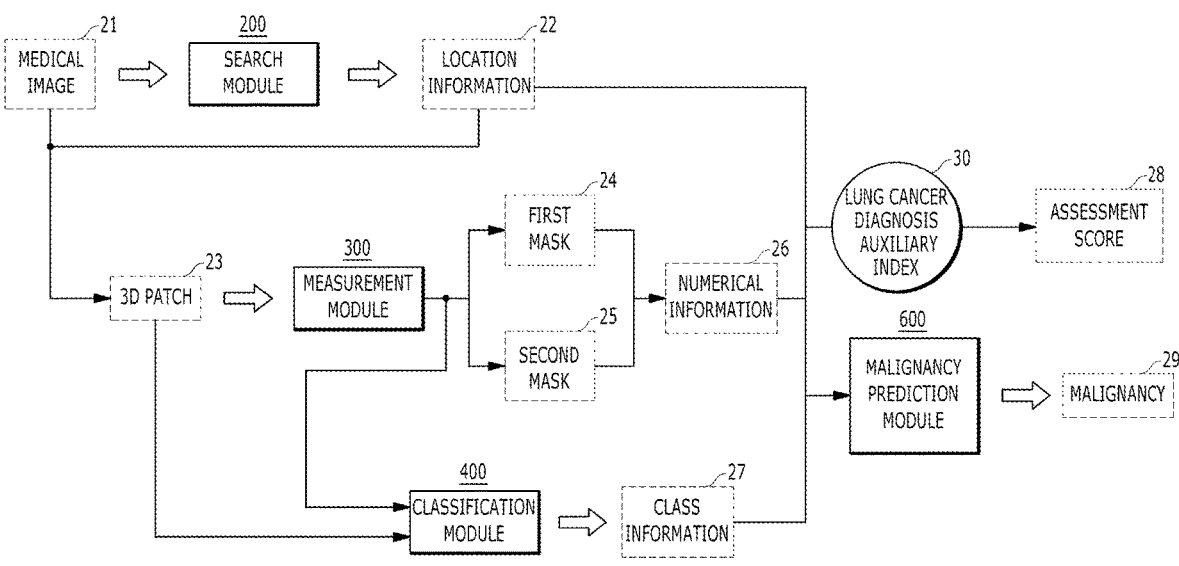
FIG. 8 is a block diagram illustrating a process of analyzing and measuring a lesion by the computing device according to an embodiment of the present disclosure.

FIG. 8 is a block diagram illustrating a process of reading and measuring a lesion by the computing device according to an embodiment of the present disclosure.

Referring to FIG. 8, the processor 110 of the computing device 100 according to an embodiment of the present disclosure may input a medical image 21 including at least one lung region into the search module 200, and generate location information 22 of the suspicious nodule present in the lung region. The processor 110 inputs a 3D patch 23 extracted from the medical image 21 based on the location information 22 of the suspicious nodule into the measurement module 300 to generate a plurality of masks 24 and 25. In this case, a first mask 24 may be a mask including information on entire region of the suspicious nodule. A second mask 25 may be a mask including information on a region in which the suspicious nodule represents a specific attribute (e.g., solid) in entire region of the suspicious nodule. The processor 110 inputs the 3D patch 23 and the plurality of masks 24 and 25 to the classification module 400 to generate class information 27 indicating the type of attribute of the suspicious nodule, whether the suspicious nodule is spiculated, whether the suspicious nodule is calcified, etc.

Meanwhile, the processor 110 may generate numerical information 26 including at least one of a diameter or a volume of the suspicious nodule based on the masks 24 and 25 for the suspicious nodule. In this case, the numerical information 26 includes first numerical information generated based on the first mask 24, and may additionally include second numerical information generated based on the second mask 25 according to a specific class of the suspicious nodule. The first numerical information may include a numerical value indicating at least one of a diameter and a volume of entire region of the suspicious nodule present in the medical image 21. The second numerical information may include a numerical value representing at least one of a diameter and a volume of a region representing a specific attribute of the suspicious nodule present in the medical image 21. The processor 110 may calculate structural numerical values related to the shape and size of a region corresponding to the suspicious nodule within the 3D patch 23 based on the information included in the first mask 24. However, when a class for a state of the suspicious nodule corresponds to a predetermined type (e.g., part-solid) for a specific attribute of the suspicious nodule, the processor 110 may calculate the above-described numerical values based on the information included in the second mask 25 jointly with the information included in the first mask 24.

The processor 110 may calculate an assessment score 28 of the suspicious nodule based on the numerical information 26 and the class information 27 based on an auxiliary index 30 of lung disease diagnosis. For example, the processor 110 reviews the numerical information 26 and the class information 27 of the suspicious nodule detected from the medical image 21 based on the auxiliary index 30 of lung cancer diagnosis to measure the suspicious nodule with one of scores defined by the auxiliary index 30. Specifically, the processor 110 may determine in which category among Lung-RADS classification categories the suspicious nodule is included based on the numerical value for the diameter and the volume of at least one of entire region of the suspicious nodule included in the numerical information 26 or the regions representing the solid attribute and information indicating the type of solid attribute included in the class information 27, whether the suspicious nodule is spiculated, or whether the suspicious nodule is calcified. When the type of solid attribute of the suspicious nodule is solid or non-solid on the class information 27, the processor 110 may determine to which category among the Lung-RADS classification categories the suspicious nodule belongs by using the first numerical information included in the numerical information 26.

When the type of solid attribute of the suspicious nodule is part-solid on the class information 27, the processor 110 may determine to which category among the Lung-RADS classification categories the suspicious nodule belongs by using both the first numerical information and the second numerical information included in the numerical information 26. Based on the result of the determination, the processor 110 may determine one of the Lung-RADS classification categories as the assessment score 28 of the suspicious nodule.

The processor 110 may predict an extent to which the suspicious nodule affects the lung as a cause of the lung disease based on the information on the suspicious nodule output through the search module 200, the measurement module 300, and the classification module 400. The processor 110 may estimate malignancy 29 of the suspicious nodule based on the location information 22, the numerical information 26, and the class information 27 of the suspicious nodule by using the pre-trained malignancy prediction module 600. For example, the processor 110 inputs a central coordinate value of the nodule included in the location information 22, a size value of the nodule included in the numerical information 26, and information on the type of solid attribute, whether the nodule is spiculated, or whether the nodule is calcified, which is included in the class information 27 into the malignancy prediction module 600 to calculate the malignancy 29 of the suspicious nodule.

Although not illustrated in FIG. 8, the processor 110 may estimate the malignancy 29 of the suspicious nodule based on the 3D patch 23 extracted from the medical image 21 and the masks 24 and 25 generated through the measurement module 300 by using the pre-trained malignancy prediction module 600. That is, the processor 110 may estimate the malignancy 29 by directly inputting quantitative information 22, 26, and 27 for the suspicious nodule extracted from the medical image 21 into the malignancy prediction module 600 and estimate the malignancy 29 by inputting image information 23, 24, and 25 generated through processing of the medical image 21 into the malignancy prediction module 600.

Figure 9:
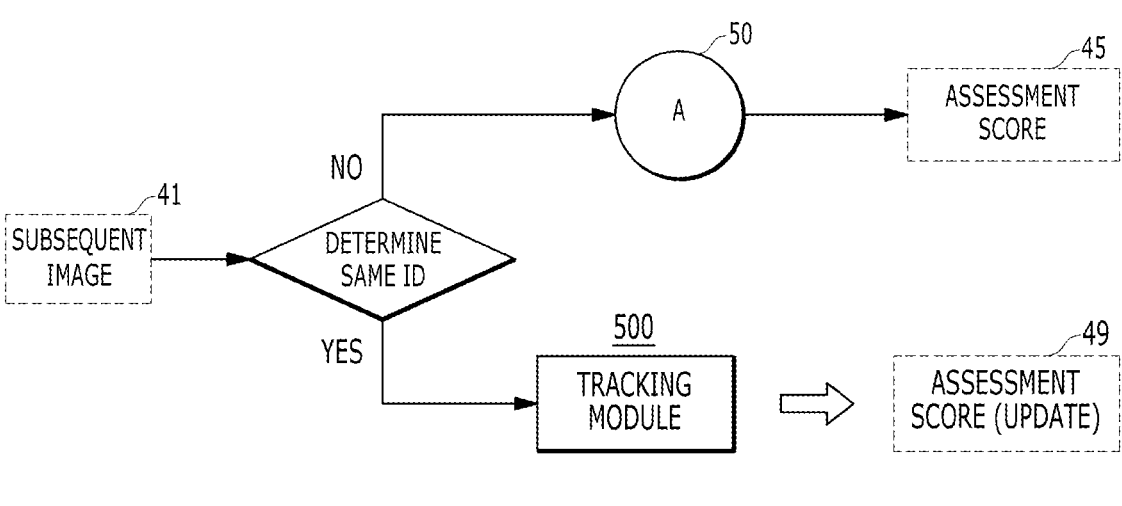
FIG. 9 is a block diagram illustrating a process of modifying a measurement result of the lesion by the computing device according to an embodiment of the present disclosure.

FIG. 9 is a block diagram illustrating a process of modifying a measurement result of the lesion by the computing device according to an embodiment of the present disclosure.

Referring to FIG. 9, the processor 110 of the computing device 100 according to an embodiment of the present disclosure may modify the assessment score for the suspicious nodule based on time-series medical images of the same subject. The processor 110 may modify the assessment score of the suspicious nodule based on a capturing time of the time-series medical images of the same subject. When the medical images are sequentially input into the computing device 100, the processor 110 may determine whether there is a history in which an image targeting the same subject as the medical image 41 is input and analyzed. When determining that there is no history for the image targeting the same subject as the medical image 41, the processor 110 may recognize the medical image 41 as a medical image for a new subject and calculate an assessment score 45 for the suspicious nodule through step A 50. In this case, step A 50 may be understood as corresponding to a calculation process of the assessment score 28 illustrated in FIG. 8.

When determining that there is a pre-analyzed image targeting the same subject as the medical image 41, the processor 110 may perform registration between the pre-analyzed image and the medical image 41 by using the pre-trained tracking module 500. Here, the registration means an operation of matching a relative positional relationship between the pre-analyzed image and the medical image 41 having a time difference. The processor 110 may match the suspicious nodule present in the pre-analyzed image and the suspicious nodule present in the medical image 41, of which registration is completed by using the tracking module 500. Although not illustrated in FIG. 9, the processor 110 may identify changed information between the matched suspicious nodules by performing step A 50 for the medical image 41. In this case, step A 50 may be understood as corresponding to the calculation process of the assessment score 28 illustrated in FIG. 8. The processor 110 may modify the assessment score of the medical image 41 or the assessment score of the pre-analyzed image based on the changed information. When the medical image 41 is captured at a time point prior to the pre-analyzed image, the processor 110 may modify the assessment score of the pre-analyzed image based on the changed information. Conversely, when the medical image 41 is captured at a time point after the pre-analyzed image, the processor 110 may modify the assessment score of the medical image based on the changed information. That is, the processor 110 compares capturing time points between the medical image 41 and the pre-analyzed image to modify the assessment score of the image captured at the most recent time point. In other words, the processor 110 may modify the assessment score of the image captured at the most recent time point in order to effectively track a temporal change of the suspicious nodule. Through this process, the processor 110 may finally generate a modified measurement score 49 of the suspicious nodule for a specific subject. Such an operation of modifying the assessment score may be repeatedly performed each time the medical image 41 is input into the computing device 100.

Figure 10:
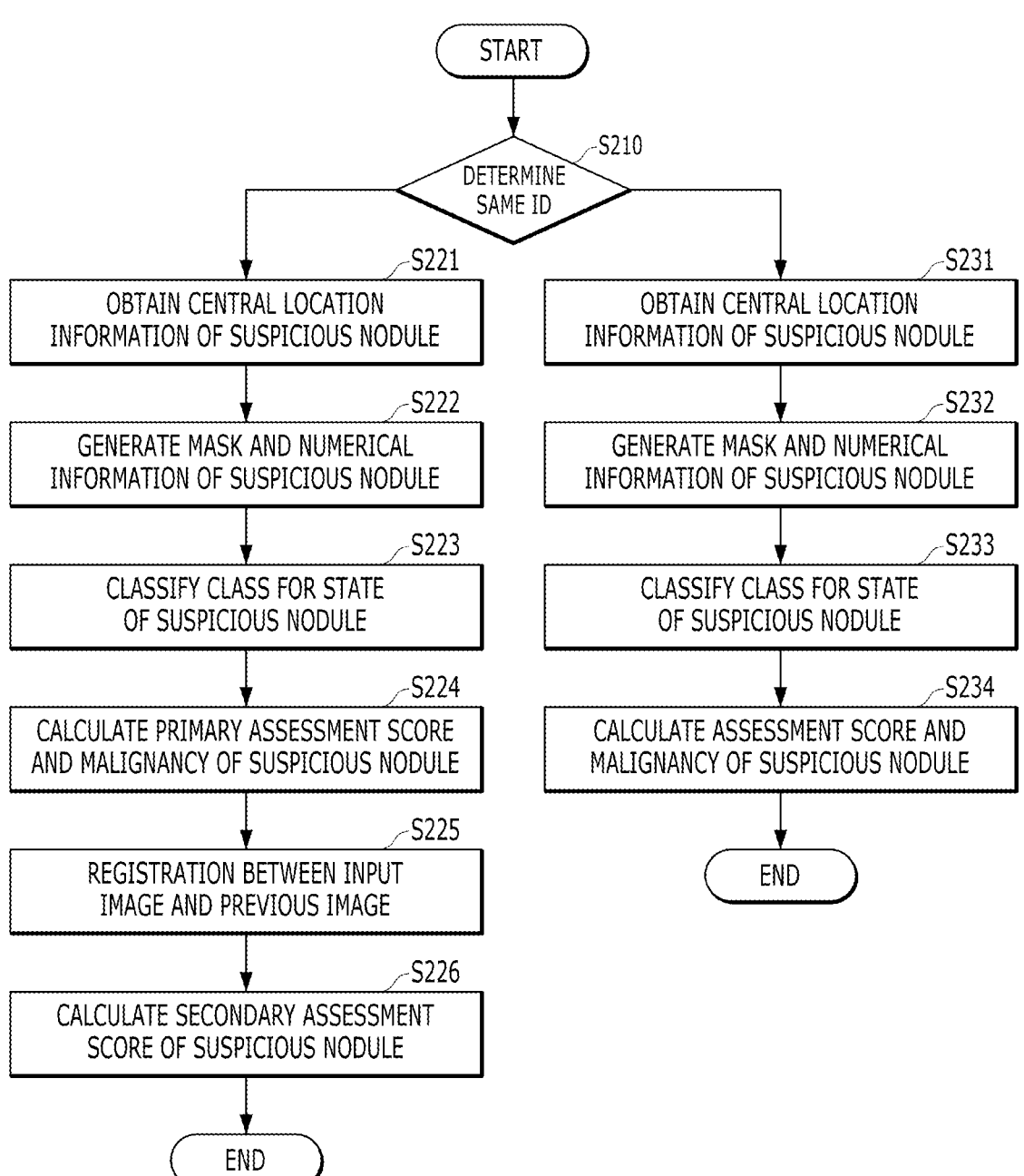
FIG. 10 is a flowchart illustrating a process of analyzing a lesion based on a medical image according to an embodiment of the present disclosure.

FIG. 10 is a flowchart illustrating a method for analyzing a lesion based on a medical image according to an embodiment of the present disclosure.

Referring to FIG. 10, in step S210, when a medical image including the chest region is input, the computing device 100 according to an embodiment of the present disclosure may determine whether there is an image having the same ID as the input image among the pre-analyzed images. Here, the ID represents identification information on a subject to be captured of the image. For example, the computing device 100 may determine whether a subject of an input CT image corresponds to a subject of a pre-analyzed CT image. When the subject of the input CT image corresponds to the subject of the pre-analyzed CT image, the computing device 100 may perform a series of operations for modifying a pre-calculated and stored measurement score of the suspicious nodule. When the subject of the input CT image does not correspond to the subject of the pre-analyzed CT image, the computing device 100 may regard that a medical image for a new subject is input, and perform a series of operations of reading and measuring the suspicious nodule based on the input CT image.

Hereinafter, a process for modifying the assessment score of the suspicious nodule, which is performed when it is determined that the subject of the input image corresponds to the subject of the existing image, will be described in general.

In step S221, the computing device 100 may obtain central location information of the suspicious nodule present in the lung tissue based on the input image. For example, the computing device 100 may generate information on a candidate region of at least one suspicious nodule based on the input image by using the pre-trained search module. The computing device 100 may generate the central location information of the suspicious nodule based on the information on the candidate region by using the search module.

In step S222, the computing device 100 may extract an image patch based on the central location information of the suspicious nodule from the input image. The computing device 100 may generate a mask of the suspicious nodule based on the image patch extracted from the input image. The computing device 100 may generate numerical information including structural numerical values of the suspicious nodule based on the mask of the suspicious nodule. For example, the computing device 100 may generate a plurality of masks for the suspicious nodule based on the image patch by using the pre-trained measurement module. The computing device 100 may generate the numerical information by calculating numerical values related to the diameter and volume of the suspicious nodule based on the information included in the plurality of masks. In this case, the numerical information may include at least one of first numerical information including structural information for entire region of the suspicious nodule or second numerical information including structural information for a region representing a specific attribute (e.g., solid) of the suspicious nodule.

In step S223, the computing device 100 may classify a class for a state of the suspicious nodule based on the image patch and the masks generated in step S222. The class related to the state of the suspicious nodule may include a first class indicating the type of attribute of the suspicious nodule, a second class indicating whether the suspicious nodule is spiculated, or a third class indicating whether the suspicious nodule is calcified. The computing device 100 may classify the state of the suspicious nodule into at least one of the first class, the second class, and the third class. For example, the computing device 100 may classify the type of solid attribute of the suspicious nodule into the solid, the part-solid, or the non-solid based on the image patch and the plurality of masks by using a first sub classification module of the classification module. The computing device 100 may classify the suspicious nodule into spiculated or non-spiculated based on the image patch and the plurality of masks by using a second sub classification module of the classification module. The computing device 100 may classify the suspicious nodule into calcification or non-calcification based on the image patch and the plurality of masks by using a third sub classification module of the classification module.

In step S224, the computing device 100 may calculate the assessment score and the malignancy of the suspicious nodule based on the central location information of the suspicious nodule generated in step S221, the numerical information generated in step S222, and the class information generated in step S223. For example, the computing device 100 may derive the assessment score of the suspicious nodule by calculating the numerical information and the class information according to a criterion defined in a predetermined diagnostic auxiliary index. The computing device 100 may estimate the malignancy of the suspicious nodule based on the central location information, the numerical information, and the class information of the suspicious nodule by using the malignancy prediction module. In addition, the computing device 100 may estimate the malignancy of the suspicious nodule based on the image patch and the mask generated in step S222 by using the malignancy prediction module.

In step S225, the computing device 100 may perform a registration of matching relative locations of the input image and the existing image. The computing device 100 may determine a change in the suspicious nodule by matching the suspicious nodule of the input image read through the above steps with the suspicious nodule of the previously read and stored image. For example, the computing device 100 may perform the registration between the input image and the existing image by using the pre-trained tracking module. The computing device 100 matches at least one suspicious nodule present in each of the two registration-completed images to determine whether a change occurs between the matched suspicious nodules.

In step S226, when it is determined that a change occurs in the matched suspicious nodule between the input image and the existing image, the computing device 100 may calculate a modified measurement score by reflecting the assessment score of the suspicious nodule derived from the input image or the assessment score of the suspicious nodule derived from the existing image to the mutual measurement score. In this case, a subject of an image in which the assessment score is modified may be determined based on a capturing time point of the image. For example, when the input image is an image of a specific subject captured in 2009 and the existing image is an image of a specific subject captured in 2015, the computing device 100 reflects the assessment score of the input image to the assessment score of the existing image to modify the assessment score of the existing image. Conversely, when the input image is the image of the specific subject captured in 2015 and the existing image is the image of the specific subject captured in 2009, the computing device 100 reflects the assessment score of the existing image to the assessment score of the input image to modify the assessment score of the input image. When it is determined that no change occurs in the matched suspicious nodule between the input image and the existing image, the computing device 100 may maintain the existing measurement score without modifying the existing measurement score.

On the other hand, steps S231 to S234 related to the process of reading and measuring the suspicious nodule, which are performed after it is determined that the subjects of the input image and the existing image do not correspond to each other, correspond to steps S221 to S224 described above, so detailed descriptions are omitted.

Figure 11:
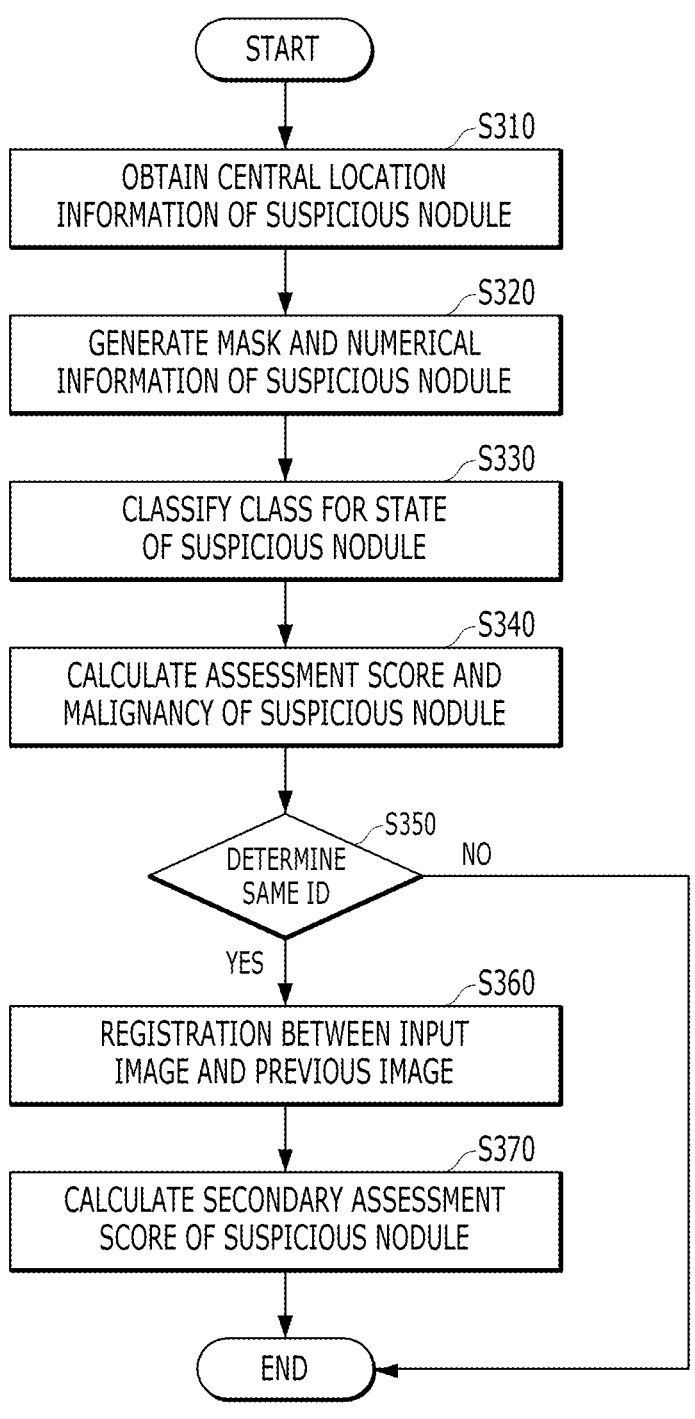
FIG. 11 is a flowchart illustrating a process of analyzing a lesion based on a medical image according to an alternative exemplary embodiment of the present disclosure.

FIG. 11 is a flowchart illustrating a method for analyzing a lesion based on a medical image according to an alternative exemplary embodiment of the present disclosure.

Referring to FIG. 11, when the medical image including the chest region is input, the computing device 100 according to an alternative embodiment of the present disclosure may first read and measure the suspicious nodule. Unlike FIG. 10, in FIG. 11, after the suspicious nodule is read and measured, it is determined whether the input image is an image captured based on the same subject as the existing image. That is, it may be understood that there is a difference between the method shown in FIG. 10 and the method shown in FIG. 11 in a precedence relationship of determination for modifying the assessment score of the suspicious nodule. Therefore, with respect to the detailed contents of respective steps (steps S310 to S370) of FIG. 11, descriptions of contents corresponding to those of FIG. 10 will be omitted.

Figure 12:
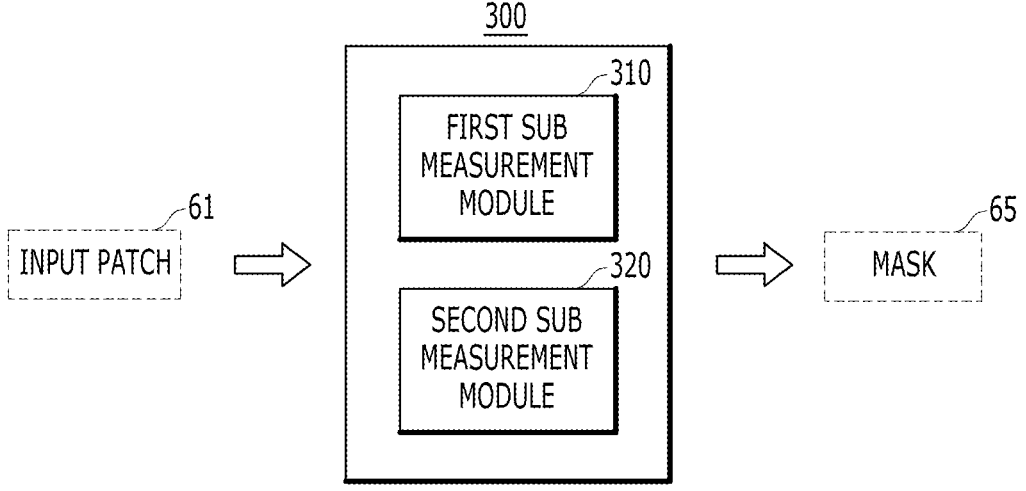
FIG. 12 is a block diagram illustrating an operation process of a measurement module included in the computing device according to an embodiment of the present disclosure.
Figure 13:
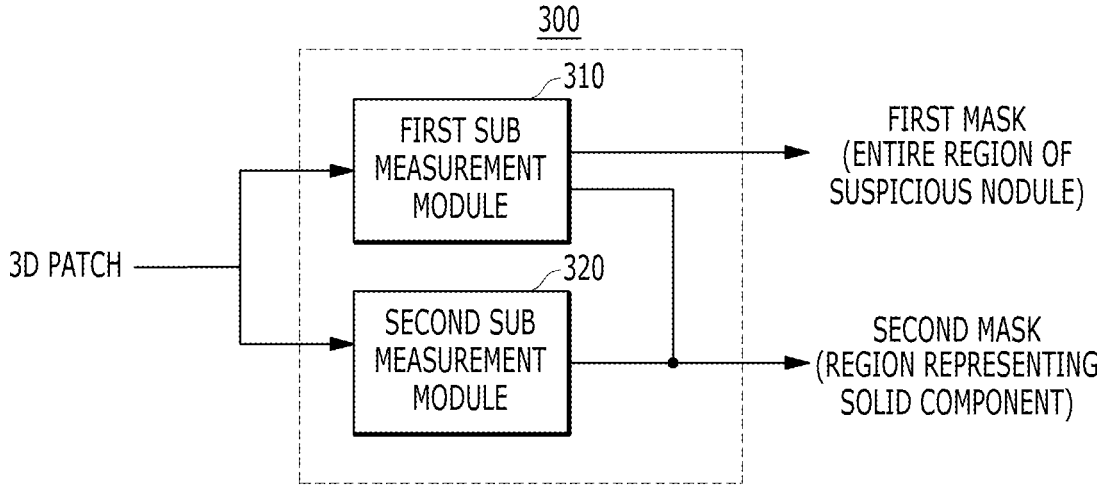
FIG. 13 is a block diagram illustrating a structure of the measurement module according to an embodiment of the present disclosure.

FIGS. 12 and 13 are block diagrams illustrating an operation process and a structure of a measurement module included in the computing device according to an embodiment of the present disclosure.

Referring to FIG. 12, the computing device 100 according to an embodiment of the present disclosure may include a measurement module 300 that generates a mask 65 of a region suspected of being a nodule from an input patch 61 on a medical image. The measurement module 300 may generate the mask 65 for the suspicious nodule by receiving the patch 61 generated from the medical image including the chest region. In this case, the computing device 100 may extract the input patch 61 of the measurement module 300 from the medical image including the chest region based on location information of the suspicious nodule. That is, the input patch 61 may be a predetermined image unit including a region corresponding to the location information of the suspicious nodule. The computing device 100 may generate the location information of the suspicious nodule used for generating the input patch 61 by using the search module 200 described with reference to FIG. 3. The computing device 100 may receive the location information itself of the suspicious nodule used for generating the input patch 61 through a user terminal, an external medical information system, etc.

The measurement module 300 may include a first sub measurement module 310 generating a first mask for entire region of the suspicious nodule based on at least one input patch 61 and a second sub measurement module 320 generating a second mask for a region representing a specific attribute of the suspicious nodule based on at least one input patch 61. The first sub measurement module 310 and the second sub measurement module 320 may perform the above-described operations through a pre-trained neural network. In this case, the neural network of each module 310 or 320 may include a convolutional neural network capable of performing segmentation regardless of the size of the input image.

Referring to FIG. 13, the first sub measurement module 310 may generate the first mask representing entire region of the suspicious nodule by receiving a 3D patch generated based on the location information of the suspicious nodule. For example, the first sub measurement module 310 may generate the first mask representing the region suspected of being the nodule in the patch by receiving the 3D patch generated based on the location information of the suspicious nodule generated through the search module 200 of FIG. 3. For example, the first sub measurement module 310 may generate the first mask representing the region suspected of being the nodule in the patch by receiving the 3D patch generated based on the location information of the suspicious nodule received from the external medical information system. In this case, the size of the 3D patch may be [32, 32, 32], but is not limited thereto.

In addition, the first sub measurement module 310 may include a neural network having a fully convolutional network (FCN) structure. Accordingly, the first sub measurement module 310 may receive the input patch regardless of the size of the input. That is, the first sub measurement module 310 combines various outputs by receiving input patches having various sizes for one suspicious nodule to generate the first mask for the suspicious nodule. For example, when the input patches having various sizes for one suspect nodule are input into the measurement module 300, the first sub measurement module 310 may generate the first sub masks for one suspicious nodule from the respective input patches. The first sub measurement module 310 may combine the first sub masks and generate the first mask for entire region of one suspicious nodule based on a result of the combination. In this case, various ensemble algorithms may be applied to a combination scheme.

The second sub measurement module 320 may generate a second mask for a region representing a solid component of the suspicious nodule by receiving the 3D patch generated based on the location information of the suspicious nodule. For example, the second sub measurement module 320 may generate the second mask for the region representing the solid component in the region suspected of being the nodule in the patch by receiving the 3D patch generated based on the location information of the suspicious nodule generated through the search module 200 of FIG. 3. The first sub measurement module 310 may generate the second mask for the region representing the solid component in the region suspected of being the nodule in the patch by receiving the 3D patch generated based on the location information of the suspicious nodule received from the external medical information system. In this case, the size of the 3D patch may be [32, 32, 32], but is not limited thereto.

Referring to FIG. 13, since the second mask for the region representing the solid component of the suspicious nodule is included in the first mask for entire region of the suspicious nodule, the second sub measurement module 320 may generate the second mask by utilizing an output result of the first sub measurement module 310. For example, the second sub measurement module 320 may generate a second sub mask for a candidate region representing the solid component of the suspicious nodule based on at least one input patch. The second sub measurement module 320 may identify an overlapping region between the first mask and the second sub mask generated through the first sub measurement module 310. The second sub measurement module 320 may generate the second mask representing the solid component of the suspicious nodule based on the identified region. In this case, a neural network structure for generating the second mask of the second sub measurement module 320 may correspond to the neural network structure of the first sub measurement module 310 described above.

On the other hand, the measurement module 300 may perform learning of the neural network by automatically selecting difficult training data that is relatively difficult to predict using online hard example mining (OHEM). The measurement module 300 is trained through the OHEM to enhance performance of identifying and extracting the suspicious nodule for mask generation.

Figure 14:
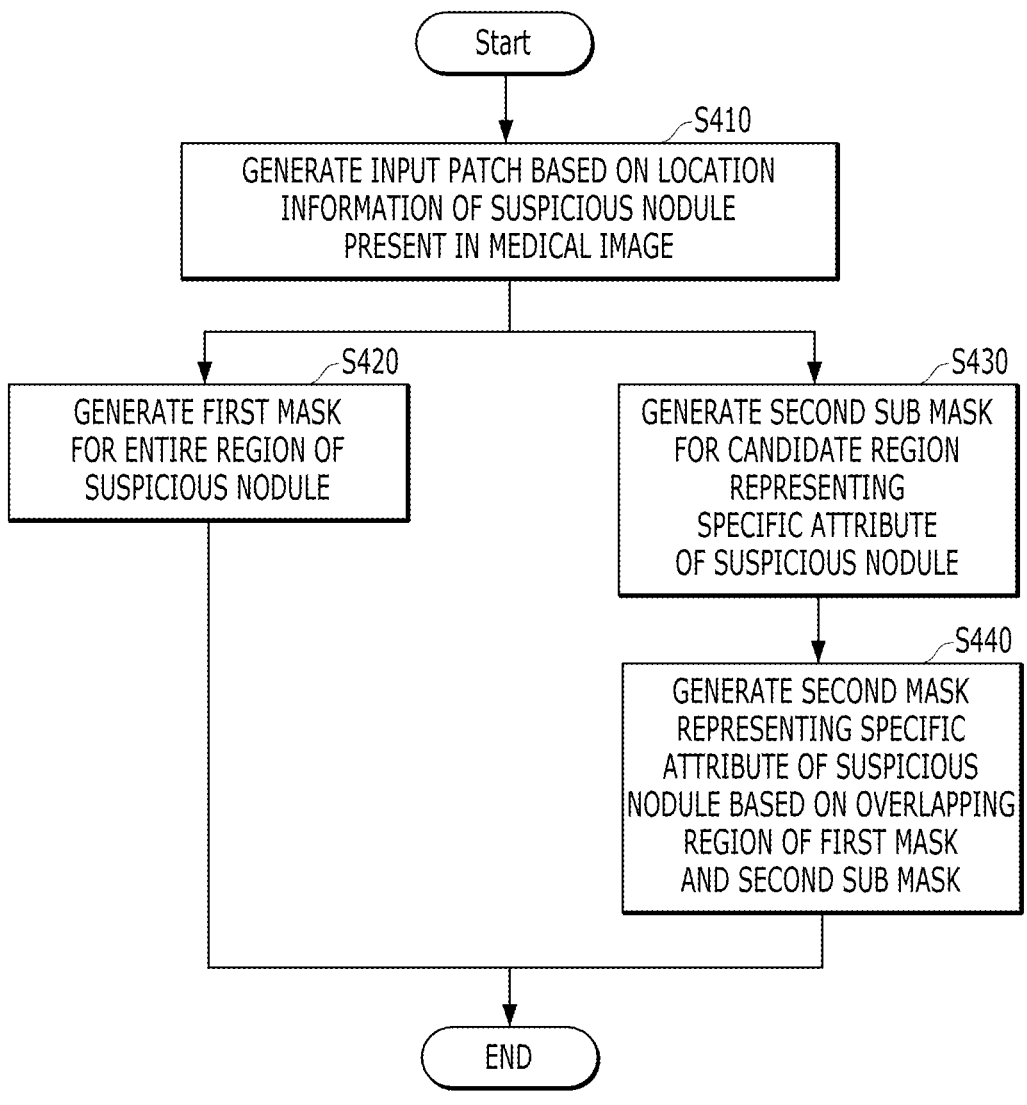
FIG. 14 is a flowchart illustrating the operation process of the measurement module according to an embodiment of the present disclosure.

FIG. 14 is a flowchart illustrating the operation process of the measurement module according to an embodiment of the present disclosure.

Referring to FIG. 14, in step S410, the computing device 100 according to an embodiment of the present disclosure may receive a medical image for lesion analysis from a medical image storage and transmission system. The medical image for lesion analysis may be a 3D CT image including a chest region. The computing device 100 may extract the location information of the suspicious nodule from the medical image through the process as shown in FIG. 7 by using the search module.

The computing device 100 may generate the input patch of the measurement module from the medical image based on the location information of the suspicious nodule. In other words, the computing device 100 may identify the location information of the suspicious nodule through analysis of the 3D CT image, and extract a 3D patch of a predetermined size including the region suspected of being the nodule from the 3D CT image. Meanwhile, as described above, the computing device 100 may directly extract the location information of the suspicious nodule by using the search module, or may receive and use the location information of the suspicious nodule through an external system.

In step S420, the computing device 100 may generate the first mask for entire region of the suspicious nodule based on the input patch by using the first sub measurement module. For example, the computing device 100 may input the 3D patch generated in step S410 into the first sub measurement module. The computing device 100 may generate the first mask representing entire region within the patch determined to be the suspicious nodule through the first sub measurement module that receives the 3D patch. In this case, the first mask may be understood as a data aggregate including meta information such as location and size of entire region of the suspicious nodule.

In step S430, the computing device 100 may generate a second sub mask for a candidate region representing a specific attribute of the suspicious nodule based on the input patch by using the second sub measurement module. For example, the computing device 100 may input the 3D patch generated in step S410 into the second sub measurement module. The computing device 100 may generate a second sub mask for a candidate region representing a solid attribute among entire region determined to be the suspicious nodule within the patch through the second sub measurement module that receives the 3D patch.

In step S440, the computing device 100 may generate the second mask for the region representing the specific attribute of the suspicious nodule based on the overlapping region of the first mask generated through step S420 and the second sub mask generated through step S430 by using the second sub measurement module. For example, the computing device 100 may identify the overlapping region between the first sub mask and the second sub mask through the second sub measurement module. The computing device 100 may finally determine the overlapping region as the region representing the solid attribute of the suspicious nodule, and generate a second mask representing the overlapping region through the second sub measurement module. In this case, the second mask may be understood as a data aggregate including meta information such as a locations and a size of the region representing the solid attribute of the suspicious nodule.

Figure 15:
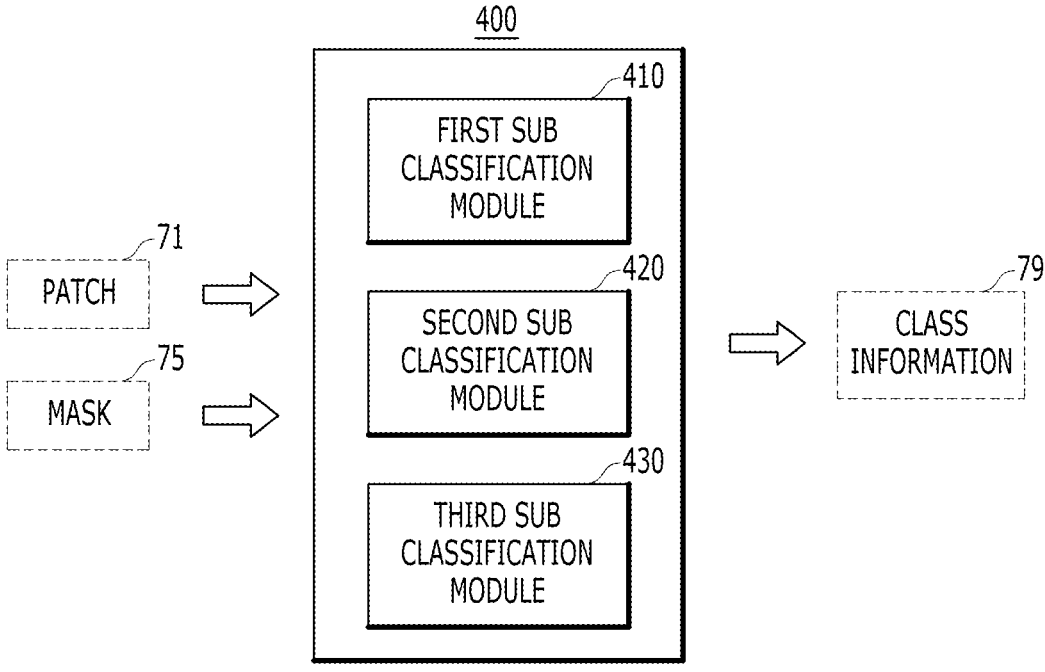
FIG. 15 is a block diagram illustrating an operation process of a classification module included in the computing device according to an embodiment of the present disclosure.
Figure 16:
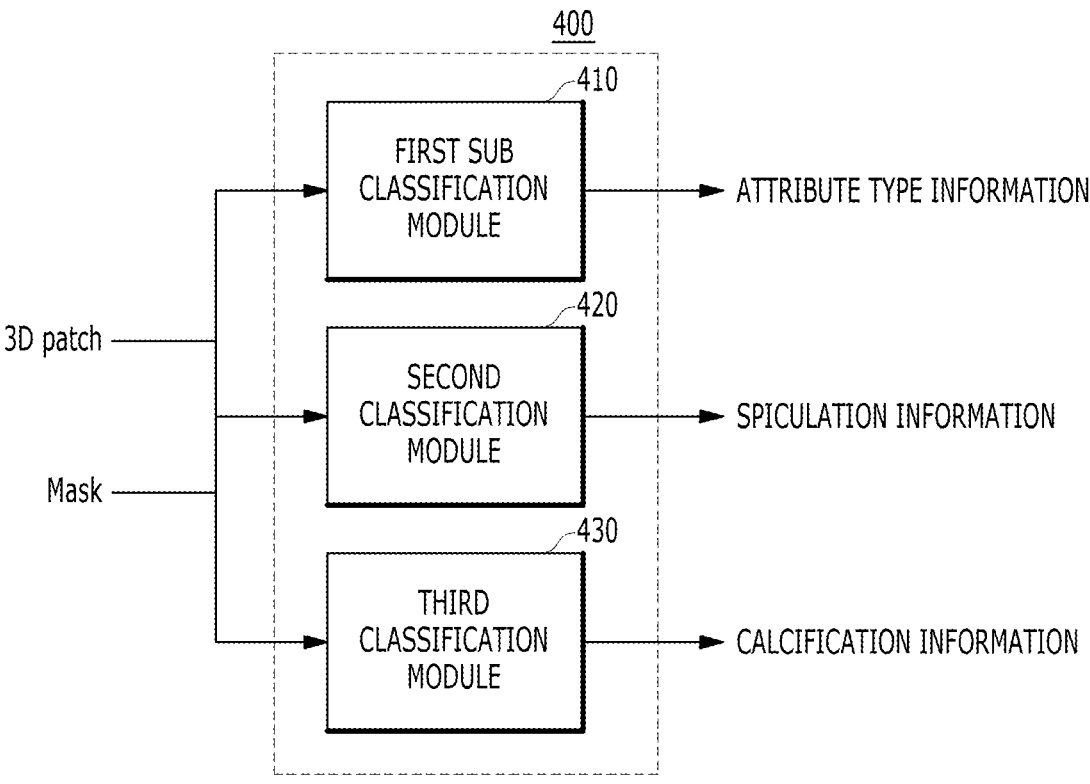
FIG. 16 is a block diagram illustrating a structure of the classification module according to an embodiment of the present disclosure.

FIGS. 15 and 16 are block diagrams illustrating an operation process and a structure of a classification module included in the computing device according to an embodiment of the present disclosure.

Referring to FIG. 15, the computing device 100 according to an embodiment of the present disclosure may include a classification module 400 that generates class information 79 for the state of the region suspected of being the nodule based on the input patch 71 of the medical image and the mask 75 for the suspicious nodule. The classification module 400 may receive the mask 75 representing the suspicious nodule together with the patch 71 generated from the medical image including the chest region, and classify a class for the state of the suspicious nodule. In this case, the computing device 100 may extract the input patch 71 of the classification module 400 from the medical image including the chest region based on the location information of the suspicious nodule. That is, the input patch 71 may be a predetermined image unit including a region corresponding to the location information of the suspicious nodule. The computing device 100 may generate the location information of the suspicious nodule used for generating the input patch 71 by using the search module 200 described with reference to FIG. 3. The computing device 100 may receive the location information itself of the suspicious nodule used for generating the input patch 71 through a user terminal, an external medical information system, etc. In addition, the computing device 100 may generate a mask 75 including at least one of entire region of the suspicious nodule or the region representing the specific attribute from the input patch 71 by using the measurement module 300 described with reference to FIG. 12.

The classification module 400 may include a first sub classification module 410 that determines the type of attribute of the suspicious nodule based on the input patch 71 generated from the medical image and the mask 75 of the suspicious nodule. The classification module 400 may include a second sub classification module 420 that determines whether the suspicious nodule is spiculated based on the input patch 71 and the mask 75. In addition, the classification module 400 may include a third sub classification module 430 that determines whether the suspicious nodule is calcified based on the input patch 71 and the mask 75. The classification module 400 may output the class information 79 by determining at least one of the type of attribute of the suspicious nodule, whether the suspicious nodule is spiculated, and whether the suspicious nodule is calcified through the respective different sub classification modules 410, 420, and 430. In this case, the second sub classification module 420 may perform the above-described operation through the pre-trained neural network.

Referring to FIG. 16, the first sub classification module 410 may receive the 3D patch generated based on the location information of the suspicious nodule and the mask of the suspicious nodule generated from the 3D patch, and classify the type of attribute of the suspicious nodule. In this case, the type of attribute of the suspicious nodule may include solid, part-solid, or non-solid. That is, the first sub-classification module 410 may determine to what extent the suspicious nodule identified in the input image contains a solid component. For example, the first sub classification module 410 may classify the type of attribute of the suspicious nodule into the solid, the part-solid, or the non-solid based on the 3D patch and the mask by using a deep learning algorithm. Further, the first sub classification module 410 may classify the type of attribute of the suspicious nodule into the solid or the non-solid based on the 3D patch and the mask based on a predetermined rule. The first sub-classification module 410 may combine a classification result based on the deep learning algorithm and a classification result based on the rule to finally determine the type of attribute of the suspicious nodule.

The second sub classification module 420 may receive the 3D patch generated based on the location information of the suspicious nodule and the mask of the suspicious nodule generated from the 3D patch, and determine whether the suspicious nodule is spiculated based on a pre-trained neural network. The neural network included in the second sub classification module 420 may include a convolutional neural network trained with a 3D feature. When the 3D patch and the mask for the suspicious nodule generated based on the 3D patch are used together, like the second sub classification module 420, classification performance for the attribute of the suspicious nodule may be increased compared to the case where only the 3D patch is used. Spiculated information of the suspicious nodule generated through the second sub classification module 420 may be used for measuring the suspicious nodule (e.g., Lung-RADS score calculation, malignancy calculation, etc.).

The third sub classification module 430 may receive the 3D patch generated based on the location information of the suspicious nodule and the mask of the suspicious nodule generated from the 3D patch, and determine whether the suspicious nodule is calcified. Specifically, the third sub classification module 430 may calculate a ratio of voxels in which a Hounsfield unit value of the voxels included in the mask is higher than a predetermined Hounsfield unit value in the 3D patch. The third sub classification module 430 may compare the ratio and the threshold value and determine whether the suspicious nodule present in the patch is calcified according to the comparison result. For example, the third sub classification module 430 may calculate the number of voxels having a predetermined Hounsfield unit value or more relative to the total number of voxels included in the mask based on the 3D patch. When the ratio of voxels calculated based on the Hounsfield unit value is higher than a specific threshold value, the third sub classification module 430 may determine that the suspicious nodule included in the 3D patch undergoes calcification. When the ratio of voxels calculated based on the Hounsfield unit value is lower than the specific threshold value, the third sub classification module 430 may determine that the suspicious nodule included in the 3D patch does not undergo calcification. Calcification information of the suspicious nodule generated through the third sub classification module 430 may be used for measuring the suspicious nodule (e.g., Lung-RADS score calculation, malignancy calculation, etc.).

Meanwhile, the third sub classification module 430 may determine whether the suspicious nodule is calcified based on the pre-trained neural network. For example, the third sub classification module 430 may receive the 3D patch and the mask and determine whether calcification of the suspicious nodule is conducted through the pre-trained neural network. Further, the third sub classification module 430 may receive the 3D patch and the mask and classify the suspicious nodule into calcification or non-calcification through the pre-trained neural network.

Figure 17:
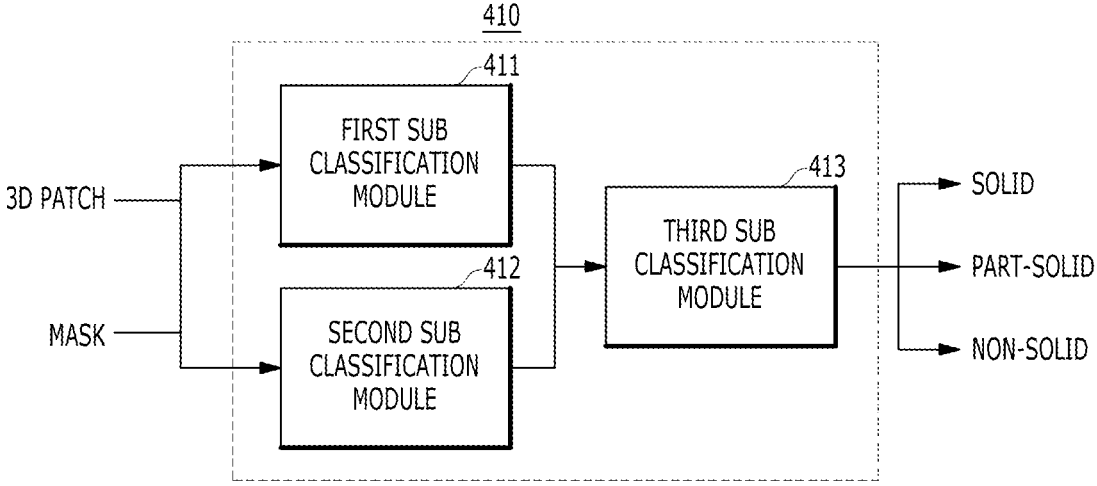
FIG. 17 is a block diagram illustrating a structure of a first sub classification module included in the classification module according to an embodiment of the present disclosure.

FIG. 17 is a block diagram illustrating a structure of a first sub classification module included in the classification module according to an embodiment of the present disclosure.

Referring to FIG. 17, the first sub classification module 410 may include a first attribute classification module 411 that receive the 3D patch generated based on the location information of the suspicious nodule and the mask of the suspicious nodule generated from the 3D patch, and determine a first type for the solid attribute of the suspicious nodule. The first sub classification module 410 may include a second attribute classification module 412 that receives the 3D patch and the mask of the suspicious nodule and determines a second type of the solid attribute of the suspicious nodule. In addition, the first sub classification module 410 may include a third attribute classification module 413 that finally determines the type for the solid attribute of the suspicious nodule based on the result of comparing the outputs of the first attribute classification module 411 and the second attribute classification module 412. In this case, the first attribute classification module 411 may perform the above-described operation through the pre-trained neural network.

The first attribute classification module 411 may receive the 3D patch generated based on the location information of the suspicious nodule and the mask of the suspicious nodule generated from the 3D patch, and determine a first type for the solid attribute of the suspicious nodule based on the pre-trained neural network. At this time, the first type may include one of the solid, the part-solid, or the non-solid. The neural network included in the first attribute classification module 411 may include a convolutional neural network trained with the 3D feature. When the 3D patch and the mask for the suspicious nodule generated based on the 3D patch are used together, like the first attribute classification module 411, the classification performance for the solid attribute of the suspicious nodule may be increased compared to the case where only the 3D patch is used. The first type of the suspicious nodule generated through the first attribute classification module 411 may be used to finally determine the type for the solid attribute of the suspicious nodule.

The second attribute classification module 412 may receive the 3D patch generated based on the location information of the suspicious nodule and the mask of the suspicious nodule generated from the 3D patch, and determine a second type for the solid attribute of the suspicious nodule. At this time, the second type may include one of the solid or the non-solid. Specifically, the second attribute classification module 412 may calculate a ratio of voxels in which a Hounsfield unit value of the voxels included in the mask is higher than a predetermined Hounsfield unit value in the 3D patch. The second attribute classification module 412 may compare the ratio and the threshold value and determine the second type of the suspicious nodule present in the patch according to the comparison result. For example, the second attribute classification module 412 may calculate the number of voxels having a predetermined Hounsfield unit value or more relative to the total number of voxels included in the mask based on the 3D patch. When the ratio of voxels calculated based on the Hounsfield unit value is higher than a specific threshold value, the second attribute classification module 412 may determine that the suspicious nodule included in the 3D patch corresponds to the solid. When the ratio of voxels calculated based on the Hounsfield unit value is lower than the specific threshold value, the second attribute classification module 412 may determine that the suspicious nodule included in the 3D patch corresponds to the non-solid. The second type of the suspicious nodule generated through the second attribute classification module 412 may be used to finally determine the type for the solid attribute of the suspicious nodule.

The third attribute classification module 413 compares the first type, which is an output of the first attribute classification module 411, and the second type, which is an output of the second attribute classification module 412, to finally determine the type related to the solid attribute of the suspicious nodule. Specifically, the third attribute classification module 413 may determine whether the first type is a type included in the second type. When the first type is not the type included in the second type, the third attribute classification module 413 may determine the first type as a final type for the solid attribute of the suspicious nodule. When the first type is the type included in the second type, the third attribute classification module 413 may determine the second type as the final type for the solid attribute of the suspicious nodule. For example, when the first type is determined as the part-solid, the first type is the type not included in the second type which is one of the solid or the non-solid, so the third attribute classification module 413 may finally determine the part-solid which is the first type as the type for the solid attribute of the suspicious nodule. When the first type is determined as one of the solid or the non-solid, the first type is the type included in the second type which is one of the solid or the non-solid, so the third attribute classification module 413 may finally determine the second type as the type for the solid attribute of the suspicious nodule.

Figure 18:
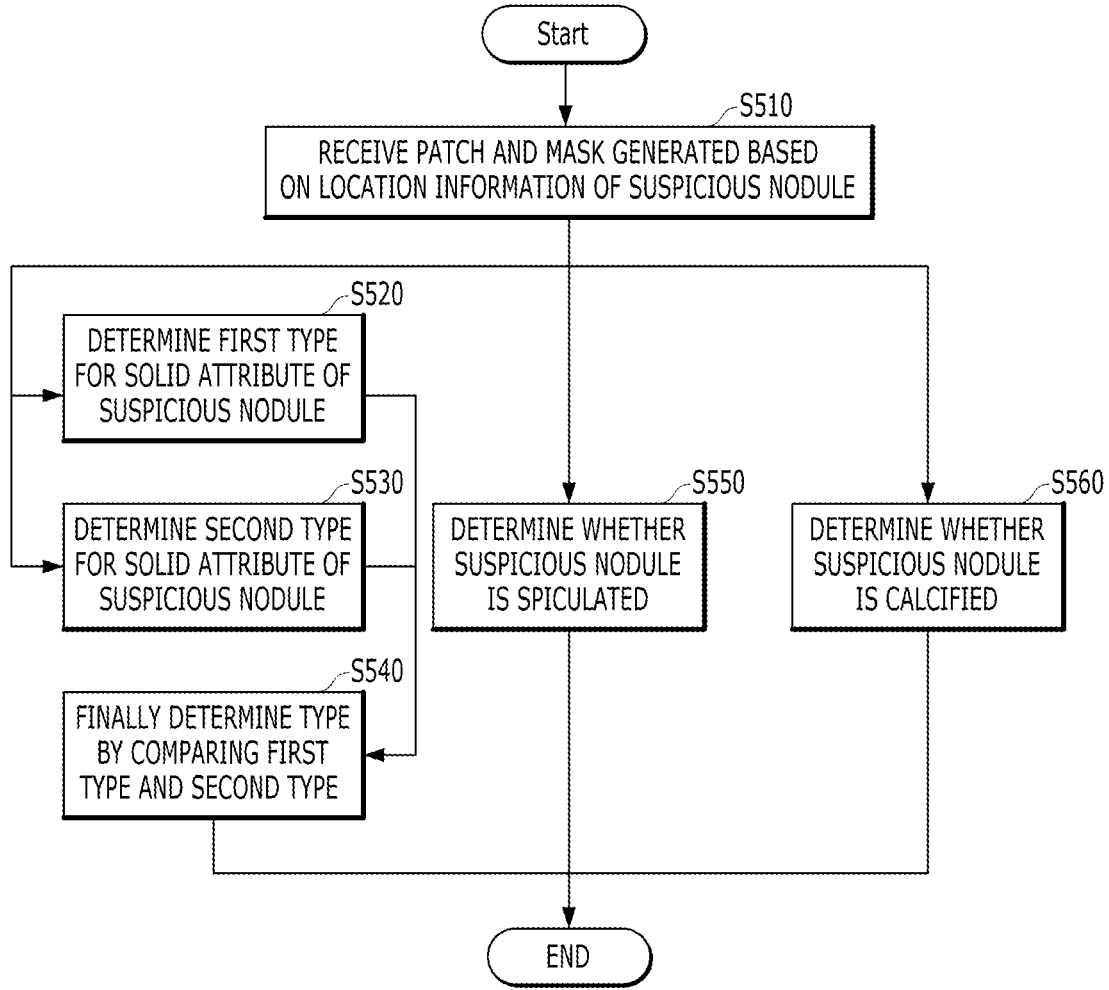
FIG. 18 is a block diagram illustrating an operation process of the classification module according to an embodiment of the present disclosure.

FIG. 18 is a block diagram illustrating an operation process of the classification module according to an embodiment of the present disclosure.

Referring to FIG. 18, in step S510, a computing device 100 according to an embodiment of the present disclosure may receive a patch generated from a medical image for lesion analysis and a mask for a lesion from an external image analysis system. The medical image for lesion analysis may be a 3D CT image including a chest region. The patch may be a 3D patch extracted from a 3D CT image based on location information of the suspicious nodule. The mask for the lesion may be a mask for at least one of entire region of the suspicious nodule generated based on the 3D patch or a region representing the solid attribute.

In step S510, the computing device 100 may receive the medical image for analyzing the lesion and may autonomously generate the patch generated from the medical image and the mask for the lesion. The computing device 100 may extract the location information of the suspicious nodule from the medical image through the process as shown in FIG. 7 by using the search module. The computing device 100 may generate the input patch of the measurement module from the medical image based on the location information of the suspicious nodule. In other words, the computing device 100 may identify the location information of the suspicious nodule through analysis of the 3D CT image, and extract a 3D patch of a predetermined size including the region suspected of being the nodule from the 3D CT image. Meanwhile, as described above, the computing device 100 may directly extract the location information of the suspicious nodule by using the search module, or may receive and use the location information of the suspicious nodule through an external system. Further, the computing device 100 may generate the mask for the suspicious nodule from the 3D patch through the process illustrated in FIG. 14 by using the measurement module.

The computing device 100 may individually perform step S520 to S540 for determining the type for the solid attribute of the suspicious nodule based on the 3D patch and the mask received or generated through step S510, step S550 for determining whether the suspicious nodule is spiculated, or step S560 for determining whether the suspicious nodule is calcified separately as necessary. The computing device 100 may generate class information utilized for measuring the suspicious nodule by individually performing the respective steps.

In step S520, the computing device 100 may determine the first type for the solid attribute of the suspicious nodule based on the patch and the mask by using the first attribute classification module pre-trained with the 3D feature. For example, the computing device 100 may input the mask generated from the 3D patch into the first attribute classification module based on the neural network jointly with the 3D patch received or generated in step S510. The computing device 100 may classify the attribute of the region determined to be the nodule in the patch into the solid, the part-solid, or the non-solid through the first attribute classification module that receives the 3D patch and the mask. Therefore, the first type may be determined as one of the solid, the part-solid, or the non-solid.

In step S530, the computing device 100 may determine the second type for the solid attribute of the suspicious nodule based on the patch and the mask by using the second attribute classification module. For example, the computing device 100 may input the mask generated from the 3D patch into the second attribute classification module based on a rule jointly with the 3D patch received or generated in step S510. The computing device 100 may classify the attribute of the region determined to be the nodule in the patch into the solid or the non-solid through the second attribute classification module that receives the 3D patch and the mask. In this case, the second attribute classification module may classify the attribute of the region determined to be the nodule in the patch into the solid or the non-solid based on the Hounsfield unit value of the voxel included in the mask. Therefore, the second type may be determined as one of the solid or the non-solid. Step S530 may be performed in parallel with step S510.

In step S540, the computing device 100 may determine the final type for the solid attribute of the suspicious nodule based on the first type determined through step S520 and the second type determined through step S530 by using the third attribute classification module. For example, the computing device 100 may compare the first type and the second type by using the third attribute classification module. When the first type is a unique type not included in one of the second types, the computing device 100 may determine the first type as the final type for the solid attribute of the suspicious nodule by using the third attribute classification module. When the first type is a type included in one of the second types, the computing device 100 may determine the second type as the final type for the solid attribute of the suspicious nodule by using the third attribute classification module.

In step S550, the computing device 100 may determine whether the suspicious nodule is spiculated based on the patch and the mask by using the second sub classification module pre-trained with the 3D feature. For example, the computing device 100 may input the mask generated from the 3D patch into the second sub classification module based on the neural network jointly with the 3D patch received or generated in step S510. The computing device 100 may determine whether the region determined to be the nodule in the patch is spiculated through the second sub classification module that receives the 3D patch and the mask. In this case, the neural network structure included in the second sub-classification module may correspond to the neural network structure included in the first attribute classification module.

In step S560, the computing device 100 may determine whether the suspicious nodule is calcified based on the patch and the mask by using the third sub classification module. For example, the computing device 100 may input the mask generated from the 3D patch into the third sub classification module based on the rule jointly with the 3D patch received or generated in step S510. The computing device 100 may determine whether the region determined to be the nodule in the patch is calcified through the third sub classification module that receives the 3D patch and the mask. In this case, the third sub classification module may determine whether the region determined to be the nodule in the patch is calcified based on the Hounsfield unit value of the voxel included in the mask. Further, the computing device 100 may input the mask generated from the 3D patch into the third sub classification module based on the deep learning algorithm jointly with the 3D patch received or generated in step S510. The computing device 100 may determine whether the region determined to be the nodule in the patch is calcified through the pre-trained third sub classification module that receives the 3D patch and the mask.

In the meantime, according to an embodiment of the present disclosure, a computer readable medium storing a data structure is disclosed.

The data structure may refer to organization, management, and storage of data that enable efficient access and modification of data. The data structure may refer to organization of data for solving a specific problem (for example, data search, data storage, and data modification in the shortest time). The data structure may also be defined with a physical or logical relationship between the data elements designed to support a specific data processing function. A logical relationship between data elements may include a connection relationship between user defined data elements. A physical relationship between data elements may include an actual relationship between the data elements physically stored in a computer readable storage medium (for example, a permanent storage device). In particular, the data structure may include a set of data, a relationship between data, and a function or a command applicable to data. Through the effectively designed data structure, the computing device may perform a calculation while minimally using resources of the computing device. In particular, the computing device may improve efficiency of calculation, reading, insertion, deletion, comparison, exchange, and search through the effectively designed data structure.

The data structure may be divided into a linear data structure and a non-linear data structure according to the form of the data structure. The linear data structure may be the structure in which only one data is connected after one data. The linear data structure may include a list, a stack, a queue, and a deque. The list may mean a series of dataset in which order exists internally. The list may include a linked list. The linked list may have a data structure in which data is connected in a method in which each data has a pointer and is linked in a single line. In the linked list, the pointer may include information about the connection with the next or previous data. The linked list may be expressed as a single linked list, a double linked list, and a circular linked list according to the form. The stack may have a data listing structure with limited access to data. The stack may have a linear data structure that may process (for example, insert or delete) data only at one end of the data structure. The data stored in the stack may have a data structure (Last In First Out, LIFO) in which the later the data enters, the sooner the data comes out. The queue is a data listing structure with limited access to data, and may have a data structure (First In First Out, FIFO) in which the later the data is stored, the later the data comes out, unlike the stack. The deque may have a data structure that may process data at both ends of the data structure.

The non-linear data structure may be the structure in which the plurality of data is connected after one data. The non-linear data structure may include a graph data structure. The graph data structure may be defined with a vertex and an edge, and the edge may include a line connecting two different vertexes. The graph data structure may include a tree data structure. The tree data structure may be the data structure in which a path connecting two different vertexes among the plurality of vertexes included in the tree is one. That is, the tree data structure may be the data structure in which a loop is not formed in the graph data structure.

Throughout the present specification, a calculation model, a nerve network, the network function, and the neural network may be used with the same meaning. Hereinafter, the terms of the calculation model, the nerve network, the network function, and the neural network are unified and described with a neural network. The data structure may include a neural network. Further, the data structure including the neural network may be stored in a computer readable medium. The data structure including the neural network may also include preprocessed data for processing by the neural network, data input to the neural network, a weight of the neural network, a hyper-parameter of the neural network, data obtained from the neural network, an active function associated with each node or layer of the neural network, and a loss function for training of the neural network. The data structure including the neural network may include predetermined configuration elements among the disclosed configurations. That is, the data structure including the neural network may include the entirety or a predetermined combination of pre-processed data for processing by neural network, data input to the neural network, a weight of the neural network, a hyper parameter of the neural network, data obtained from the neural network, an active function associated with each node or layer of the neural network, and a loss function for training the neural network. In addition to the foregoing configurations, the data structure including the neural network may include predetermined other information determining a characteristic of the neural network. Further, the data structure may include all type of data used or generated in a computation process of the neural network, and is not limited to the foregoing matter. The computer readable medium may include a computer readable recording medium and/or a computer readable transmission medium. The neural network may be formed of a set of interconnected calculation units which are generally referred to as "nodes". The "nodes" may also be called "neurons." The neural network consists of one or more nodes.

The data structure may include data input to the neural network. The data structure including the data input to the neural network may be stored in the computer readable medium. The data input to the neural network may include training data input in the training process of the neural network and/or input data input to the training completed neural network. The data input to the neural network may include data that has undergone pre-processing and/or data to be pre-processed. The pre-processing may include a data processing process for inputting data to the neural network. Accordingly, the data structure may include data to be pre-processed and data generated by the pre-processing. The foregoing data structure is merely an example, and the present disclosure is not limited thereto.

The data structure may include a weight of the neural network (in the present specification, weights and parameters may be used with the same meaning), Further, the data structure including the weight of the neural network may be stored in the computer readable medium. The neural network may include a plurality of weights. The weight is variable, and in order for the neural network to perform a desired function, the weight may be varied by a user or an algorithm. For example, when one or more input nodes are connected to one output node by links, respectively, the output node may determine a data value output from the output node based on values input to the input nodes connected to the output node and the weight set in the link corresponding to each of the input nodes. The foregoing data structure is merely an example, and the present disclosure is not limited thereto.

For a non-limited example, the weight may include a weight varied in the neural network training process and/or the weight when the training of the neural network is completed. The weight varied in the neural network training process may include a weight at a time at which a training cycle starts and/or a weight varied during a training cycle. The weight when the training of the neural network is completed may include a weight of the neural network completing the training cycle. Accordingly, the data structure including the weight of the neural network may include the data structure including the weight varied in the neural network training process and/or the weight when the training of the neural network is completed. Accordingly, it is assumed that the weight and/or a combination of the respective weights are included in the data structure including the weight of the neural network. The foregoing data structure is merely an example, and the present disclosure is not limited thereto.

The data structure including the weight of the neural network may be stored in the computer readable storage medium (for example, a memory and a hard disk) after undergoing a serialization process. The serialization may be the process of storing the data structure in the same or different computing devices and converting the data structure into a form that may be reconstructed and used later. The computing device may serialize the data structure and transceive the data through a network. The serialized data structure including the weight of the neural network may be reconstructed in the same or different computing devices through deserialization. The data structure including the weight of the neural network is not limited to the serialization. Further, the data structure including the weight of the neural network may include a data structure (for example, in the non-linear data structure, B-Tree, Trie, m-way search tree, AVL tree, and Red-Black Tree) for improving efficiency of the calculation while minimally using the resources of the computing device. The foregoing matter is merely an example, and the present disclosure is not limited thereto.

The data structure may include a hyper-parameter of the neural network. The data structure including the hyper-parameter of the neural network may be stored in the computer readable medium. The hyper-parameter may be a variable varied by a user. The hyper-parameter may include, for example, a learning rate, a cost function, the number of times of repetition of the training cycle, weight initialization (for example, setting of a range of a weight value to be weight-initialized), and the number of hidden units (for example, the number of hidden layers and the number of nodes of the hidden layer). The foregoing data structure is merely an example, and the present disclosure is not limited thereto.

Figure 19:
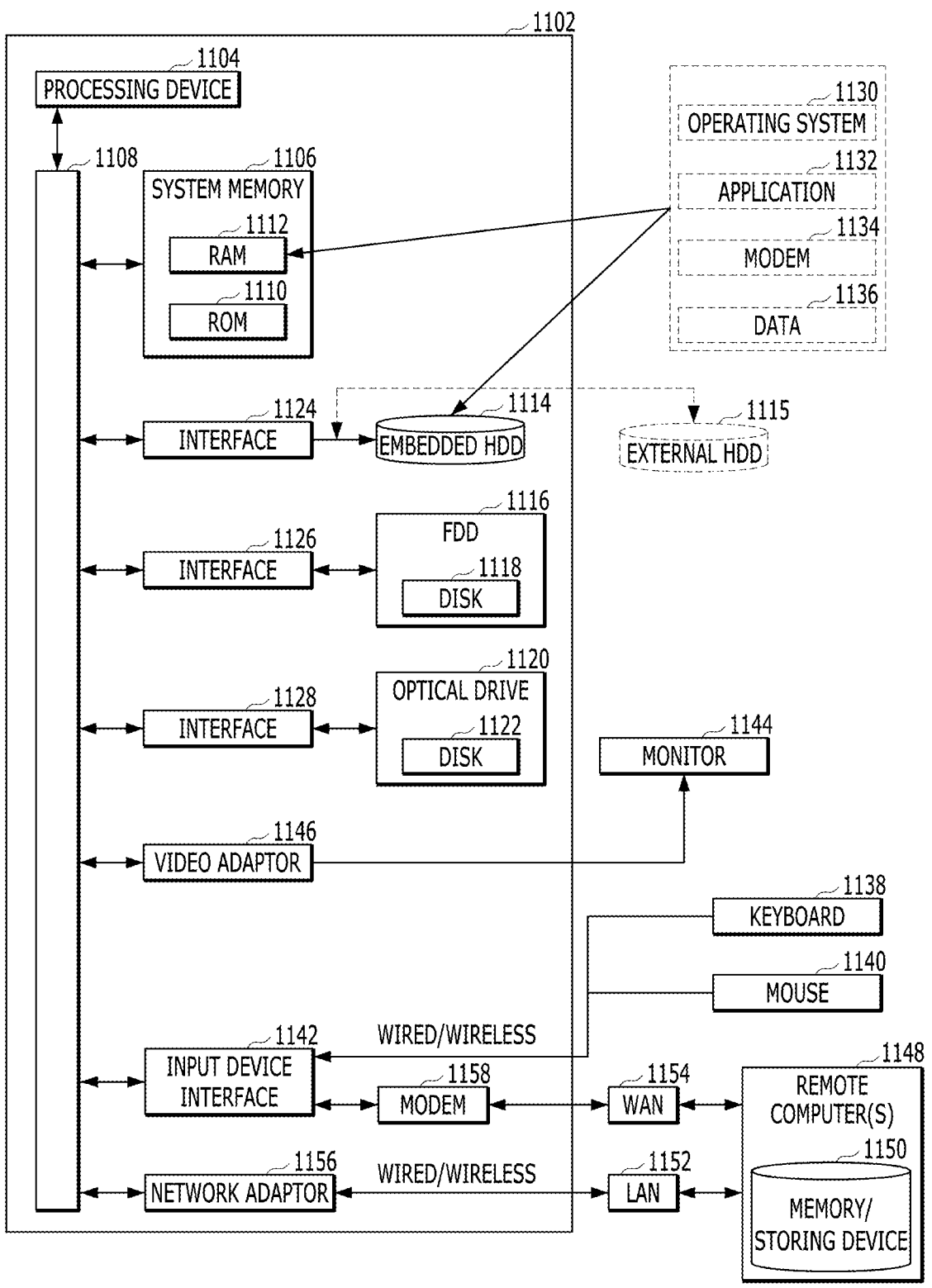
FIG. 19 is a schematic diagram of a computing environment according to an embodiment of the present disclosure.

FIG. 19 is a simple and general schematic diagram illustrating an example of a computing environment in which the embodiments of the present disclosure are implementable.

The present disclosure has been described as being generally implementable by the computing device, but those skilled in the art will appreciate well that the present disclosure is combined with computer executable commands and/or other program modules executable in one or more computers and/or be implemented by a combination of hardware and software.

In general, a program module includes a routine, a program, a component, a data structure, and the like performing a specific task or implementing a specific abstract data form. Further, those skilled in the art will well appreciate that the method of the present disclosure may be carried out by a personal computer, a hand-held computing device, a microprocessor-based or programmable home appliance (each of which may be connected with one or more relevant devices and be operated), and other computer system configurations, as well as a single-processor or multiprocessor computer system, a mini computer, and a main frame computer.

The embodiments of the present disclosure may be carried out in a distribution computing environment, in which certain tasks are performed by remote processing devices connected through a communication network. In the distribution computing environment, a program module may be located in both a local memory storage device and a remote memory storage device.

The computer generally includes various computer readable media. The computer accessible medium may be any type of computer readable medium, and the computer readable medium includes volatile and non-volatile media, transitory and non-transitory media, and portable and non-portable media. As a non-limited example, the computer readable medium may include a computer readable storage medium and a computer readable transport medium. The computer readable storage medium includes volatile and non-volatile media, transitory and non-transitory media, and portable and non-portable media constructed by a predetermined method or technology, which stores information, such as a computer readable command, a data structure, a program module, or other data. The computer readable storage medium includes a RAM, a Read Only Memory (ROM), an Electrically Erasable and Programmable ROM (EEPROM), a flash memory, or other memory technologies, a Compact Disc (CD)-ROM, a Digital Video Disk (DVD), or other optical disk storage devices, a magnetic cassette, a magnetic tape, a magnetic disk storage device, or other magnetic storage device, or other predetermined media, which are accessible by a computer and are used for storing desired information, but is not limited thereto.

The computer readable transport medium generally implements a computer readable command, a data structure, a program module, or other data in a modulated data signal, such as a carrier wave or other transport mechanisms, and includes all of the information transport media. The modulated data signal means a signal, of which one or more of the characteristics are set or changed so as to encode information within the signal. As a non-limited example, the computer readable transport medium includes a wired medium, such as a wired network or a direct-wired connection, and a wireless medium, such as sound, Radio Frequency (RF), infrared rays, and other wireless media. A combination of the predetermined media among the foregoing media is also included in a range of the computer readable transport medium.

An illustrative environment 1100 including a computer 1102 and implementing several aspects of the present disclosure is illustrated, and the computer 1102 includes a processing device 1104, a system memory 1106, and a system bus 1108. The system bus 1108 connects system components including the system memory 1106 (not limited) to the processing device 1104. The processing device 1104 may be a predetermined processor among various commonly used processors. A dual processor and other multi-processor architectures may also be used as the processing device 1104.

The system bus 1108 may be a predetermined one among several types of bus structure, which may be additionally connectable to a local bus using a predetermined one among a memory bus, a peripheral device bus, and various common bus architectures. The system memory 1106 includes a ROM 1110, and a RAM 1112. A basic input/output system (BIOS) is stored in a non-volatile memory 1110, such as a ROM, an EPROM, and an EEPROM, and the BIOS includes a basic routing helping a transport of information among the constituent elements within the computer 1102 at a time, such as starting. The RAM 1112 may also include a high-rate RAM, such as a static RAM, for caching data.

The computer 1102 also includes an embedded hard disk drive (HDD) 1114 (for example, enhanced integrated drive electronics (EIDE) and serial advanced technology attachment (SATA))—the embedded HDD 1114 being configured for exterior mounted usage within a proper chassis (not illustrated)—a magnetic floppy disk drive (FDD) 1116 (for example, which is for reading data from a portable diskette 1118 or recording data in the portable diskette 1118), and an optical disk drive 1120 (for example, which is for reading a CD-ROM disk 1122, or reading data from other high-capacity optical media, such as a DVD, or recording data in the high-capacity optical media). A hard disk drive 1114, a magnetic disk drive 1116, and an optical disk drive 1120 may be connected to a system bus 1108 by a hard disk drive interface 1124, a magnetic disk drive interface 1126, and an optical drive interface 1128, respectively. An interface 1124 for implementing an outer mounted drive includes, for example, at least one of or both a universal serial bus (USB) and the Institute of Electrical and Electronics Engineers (IEEE) 1394 interface technology.

The drives and the computer readable media associated with the drives provide non-volatile storage of data, data structures, computer executable commands, and the like. In the case of the computer 1102, the drive and the medium correspond to the storage of random data in an appropriate digital form. In the description of the computer readable media, the HDD, the portable magnetic disk, and the portable optical media, such as a CD, or a DVD, are mentioned, but those skilled in the art will well appreciate that other types of computer readable media, such as a zip drive, a magnetic cassette, a flash memory card, and a cartridge, may also be used in the illustrative operation environment, and the predetermined medium may include computer executable commands for performing the methods of the present disclosure.

A plurality of program modules including an operation system 1130, one or more application programs 1132, other program modules 1134, and program data 1136 may be stored in the drive and the RAM 1112. An entirety or a part of the operation system, the application, the module, and/or data may also be cached in the RAM 1112. It will be well appreciated that the present disclosure may be implemented by several commercially usable operation systems or a combination of operation systems.

A user may input a command and information to the computer 1102 through one or more wired/wireless input devices, for example, a keyboard 1138 and a pointing device, such as a mouse 1140. Other input devices (not illustrated) may be a microphone, an IR remote controller, a joystick, a game pad, a stylus pen, a touch screen, and the like. The foregoing and other input devices are frequently connected to the processing device 1104 through an input device interface 1142 connected to the system bus 1108, but may be connected by other interfaces, such as a parallel port, an IEEE 1394 serial port, a game port, a USB port, an IR interface, and other interfaces.

A monitor 1144 or other types of display devices are also connected to the system bus 1108 through an interface, such as a video adaptor 1146. In addition to the monitor 1144, the computer generally includes other peripheral output devices (not illustrated), such as a speaker and a printer. The computer 1102 may be operated in a networked environment by using a logical connection to one or more remote computers, such as remote computer(s) 1148, through wired and/or wireless communication. The remote computer(s) 1148 may be a workstation, a computing device computer, a router, a personal computer, a portable computer, a microprocessor-based entertainment device, a peer device, and other general network nodes, and generally includes some or an entirety of the constituent elements described for the computer 1102, but only a memory storage device 1150 is illustrated for simplicity. The illustrated logical connection includes a wired/wireless connection to a local area network (LAN) 1152 and/or a larger network, for example, a wide area network (WAN) 1154. The LAN and WAN networking environments are general in an office and a company, and make an enterprise-wide computer network, such as an Intranet, easy, and all of the LAN and WAN networking environments may be connected to a worldwide computer network, for example, the Internet.

When the computer 1102 is used in the LAN networking environment, the computer 1102 is connected to the local network 1152 through a wired and/or wireless communication network interface or an adaptor 1156. The adaptor 1156 may make wired or wireless communication to the LAN 1152 easy, and the LAN 1152 also includes a wireless access point installed therein for the communication with the wireless adaptor 1156. When the computer 1102 is used in the WAN networking environment, the computer 1102 may include a modem 1158, is connected to a communication computing device on a WAN 1154, or includes other means setting communication through the WAN 1154 via the Internet. The modem 1158, which may be an embedded or outer-mounted and wired or wireless device, is connected to the system bus 1108 through a serial port interface 1142. In the networked environment, the program modules described for the computer 1102 or some of the program modules may be stored in a remote memory/storage device 1150. The illustrated network connection is illustrative, and those skilled in the art will appreciate well that other means setting a communication link between the computers may be used.

The computer 1102 performs an operation of communicating with a predetermined wireless device or entity, for example, a printer, a scanner, a desktop and/or portable computer, a portable data assistant (PDA), a communication satellite, predetermined equipment or place related to a wirelessly detectable tag, and a telephone, which is disposed by wireless communication and is operated. The operation includes a wireless fidelity (Wi-Fi) and Bluetooth wireless technology at least. Accordingly, the communication may have a pre-defined structure, such as a network in the related art, or may be simply ad hoc communication between at least two devices.

The Wi-Fi enables a connection to the Internet and the like even without a wire. The Wi-Fi is a wireless technology, such as a cellular phone, which enables the device, for example, the computer, to transmit and receive data indoors and outdoors, that is, in any place within a communication range of a base station. A Wi-Fi network uses a wireless technology, which is called IEEE 802.11 (a, b, g, etc.) for providing a safe, reliable, and high-rate wireless connection. The Wi-Fi may be used for connecting the computer to the computer, the Internet, and the wired network (IEEE 802.3 or Ethernet is used). The Wi-Fi network may be operated at, for example, a data rate of 11 Mbps (802.11a) or 54 Mbps (802.11b) in an unauthorized 2.4 and 5 GHz wireless band, or may be operated in a product including both bands (dual bands).

Those skilled in the art may appreciate that information and signals may be expressed by using predetermined various different technologies and techniques. For example, data, indications, commands, information, signals, bits, symbols, and chips referable in the foregoing description may be expressed with voltages, currents, electromagnetic waves, magnetic fields or particles, optical fields or particles, or a predetermined combination thereof.

Those skilled in the art will appreciate that the various illustrative logical blocks, modules, processors, means, circuits, and algorithm operations described in relationship to the embodiments disclosed herein may be implemented by electronic hardware (for convenience, called "software" herein), various forms of program or design code, or a combination thereof. In order to clearly describe compatibility of the hardware and the software, various illustrative components, blocks, modules, circuits, and operations are generally illustrated above in relation to the functions of the hardware and the software. Whether the function is implemented as hardware or software depends on design limits given to a specific application or an entire system. Those skilled in the art may perform the function described by various schemes for each specific application, but it shall not be construed that the determinations of the performance depart from the scope of the present disclosure.

Various embodiments presented herein may be implemented by a method, a device, or a manufactured article using a standard programming and/or engineering technology. A term "manufactured article" includes a computer program, a carrier, or a medium accessible from a predetermined computer-readable storage device. For example, the computer-readable storage medium includes a magnetic storage device (for example, a hard disk, a floppy disk, and a magnetic strip), an optical disk (for example, a CD and a DVD), a smart card, and a flash memory device (for example, an EEPROM, a card, a stick, and a key drive), but is not limited thereto. Further, various storage media presented herein include one or more devices and/or other machine-readable media for storing information.

It shall be understood that a specific order or a hierarchical structure of the operations included in the presented processes is an example of illustrative accesses. It shall be understood that a specific order or a hierarchical structure of the operations included in the processes may be rearranged within the scope of the present disclosure based on design priorities. The accompanying method claims provide various operations of elements in a sample order, but it does not mean that the claims are limited to the presented specific order or hierarchical structure.

The description of the presented embodiments is provided so as for those skilled in the art to use or carry out the present disclosure. Various modifications of the embodiments may be apparent to those skilled in the art, and general principles defined herein may be applied to other embodiments without departing from the scope of the present disclosure. Accordingly, the present disclosure is not limited to the embodiments suggested herein, and shall be interpreted within the broadest meaning range consistent to the principles and new characteristics presented herein.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for analyzing a lesion based on a medical image performed by a computing device including at least one processor, the method comprising:

generating, input image data comprising 2D medical images and a 3D medical image from the medical image;

generating, from the 2D medical images, a first probability value regarding a presence of a nodule in at least one region of interest and first location information identifying the at least one region of interest, estimating a second probability value regarding the at least one region of interest based on the 3D medical image and the first location information; and determining, second location information for the nodule from the first location information, based on the first probability value and the second probability value.

2. The method of claim 1, wherein the generating of the input image data includes:

calculating a Hounsfield unit value based on a 3D medical image; and generating the 2D medical images from the 3D medical image in which the Hounsfield unit value is calculated.

3. The method of claim 1, wherein the generating of the first probability value and the first location information includes:

generating first feature maps having a plurality of sizes based on the 2D medical images by using a first neural network module;

generating second feature maps by concatenating at least some of the first feature maps based on the sizes of the first feature maps by using a second neural network module; and generating the first probability value and the first location information regarding the at least one region of interest by matching the second feature maps with a predetermined anchor box by using a third neural network module.

4. The method of claim 3, wherein the generating of the first probability value and the first location information further includes:

clustering, when there is a plurality of regions of interest, at least some of the regions of interest based on a ratio of overlapping regions between the plurality of regions of interest; and correcting a coordinate included in the first location information.

5. The method of claim 1, wherein the estimating of the second probability value includes:

generating at least one third feature map by performing encoding based on a patch extracted from the 3D medical image based on the first location information by using a fourth neural network module;

generating at least one fourth feature map by performing decoding based on the third feature map by using a fifth neural network module; and generating the second probability value regarding the at least one region of interest based on a feature map generated by combining the third feature map and the fourth feature map by using a sixth neural network module.

6. The method of claim 1, wherein the estimating of the second probability value is performed by a neural network that is pre-trained by performing, a first operation of training the neural network based on a randomly sampled training image, and a second operation of training the neural network based on a training image selected based on recall and precision.

7. The method of claim 1, wherein the determining of the second location information for the nodule includes:

comparing a third probability value regarding the presence of the nodule generated through a weighted sum of the first probability value and the second probability value, and a threshold value; and determining the first location information of the at least one region of interest corresponding to the third probability value regarding the presence of the nodule selected as a result of the comparison as the second location information for the nodule.

8. The method of claim 1, further comprising:

generating a mask for the nodule based on a patch of the medical image corresponding to the second location information by using a pre-trained measurement module; and generating numerical information including at least one of a diameter and a volume of the nodule based on the mask for the nodule.

9. The method of claim 8, wherein the mask for the suspicious nodule includes:

a first mask for an entire region of the nodule generated based on a 3D patch corresponding to the second location information; and a second mask for a region representing a specific attribute of the nodule generated based on the 3D patch corresponding to the second location information.

10. The method of claim 8, further comprising:

classifying a class for a state of the nodule based on the patch of the medical image and the mask for the nodule by using a pre-trained classification module.

11. The method of claim 10, wherein the classifying of the class for the state of the nodule includes:

determining at least one of a type for an attribute of the nodule, whether the nodule is spiculated, or whether the nodule is calcified, based on the patch and the mask by using different sub modules included in the classification module.

12. The method of claim 10, further comprising:

calculating an assessment score of the nodule based on the numerical information and the class for the state of the nodule based on an auxiliary index of lung cancer diagnosis; and modifying, when a subject of the input image data corresponds to a subject of a pre-analyzed image, an assessment score of the medical image or an assessment score of the pre-analyzed image based on capturing time points of the input image data and the pre-analyzed image by using a pre-trained tracking module.

13. The method of claim 12, further comprising:

generating a user interface based on at least one of the second location information, the mask, the class, the numerical information, or the assessment score for the nodule.

14. The method of claim 10, further comprising:

estimating malignancy of the nodule by inputting the second location information, the class for the state, and the numerical information of the nodule into a pre-trained machine learning module.

15. The method of claim 14, further comprising:

generating a user interface based on at least one of the second location information, the mask, the class, the numerical information, or the malignancy for the nodule.

16. The method of claim 10, further comprising:

estimating malignancy of the nodule by inputting the patch of the medical image and the mask for the nodule into a pre-trained machine learning module.

17. A computer program stored in a non-transitory computer-readable storage medium, the computer program executing following operations for analyzing a lesion based on a medical image when the computer program is executed by one or more processors, the operations comprising:

an operation of generating, input image data comprising 2D medical images and a 3D medical image from the medical image;

an operation of generating, from the 2D medical images a first probability value regarding a presence of a nodule in at least one region of interest and first location information identifying the at least one region of interest;

an operation of estimating a second probability value regarding the at least one region of interest based on the 3D medical image and the first location information; and an operation of determining, second location information for the nodule from the first location information, based on the first probability value and the second probability value.

18. A computing device for analyzing a lesion based on a medical image, comprising:

a processor including at least one core;

a memory including program codes executable in the processor; and a network unit receiving a medical image, wherein the processor, generates, input image data comprising 2D medical images and a 3D medical image from the medical image, generates, from the 2D medical images, a first probability value regarding a presence of a nodule in at least one region of interest and first location information identifying the at least one region of interest, estimates a second probability value regarding the at least one region of interest based on the 3D medical image and the first location information, and determines, second location information for the nodule from the first location information, based on the first probability value and the second probability value.

* * * * *